US010861601B2

(12) United States Patent
Gutekunst et al.

(10) Patent No.: US 10,861,601 B2
(45) Date of Patent: Dec. 8, 2020

(54) SYSTEM AND METHOD FOR MEDICAL SURVEILLANCE THROUGH PERSONAL COMMUNICATION DEVICE

(71) Applicant: TOUCHDX, San Diego, CA (US)

(72) Inventors: Brent Gutekunst, San Diego, CA (US); Darin Okuda, San Diego, CA (US); Laurie Babb, San Diego, CA (US); Vic Markarian, San Diego, CA (US)

(73) Assignee: TOUCHDX, San Diego, CA (US)

( * ) Notice: Subject to any disclaimer, the term of this patent is extended or adjusted under 35 U.S.C. 154(b) by 579 days.

(21) Appl. No.: 15/356,342

(22) Filed: Nov. 18, 2016

(65) Prior Publication Data

US 2017/0124278 A1 May 4, 2017

Related U.S. Application Data

(63) Continuation of application No. 12/906,450, filed on Oct. 18, 2010, now abandoned.

(60) Provisional application No. 61/348,367, filed on May 26, 2010, provisional application No. 61/327,386, filed on Apr. 23, 2010, provisional application No. 61/321,568, filed on Apr. 7, 2010, provisional application No. 61/312,943, filed on Mar. 11, 2010, provisional application No. 61/299,568, filed on Jan. 29, 2010, provisional application No. 61/298,077, filed on Jan. 25, 2010, provisional application No. 61/298,068, filed on Jan. 25, 2010, provisional (Continued)

(51) Int. Cl.
G06F 21/62 (2013.01)
G16H 40/63 (2018.01)
G06F 19/00 (2018.01)

(52) U.S. Cl.
CPC .......... *G16H 40/63* (2018.01); *G06F 19/3418* (2013.01); *G06F 21/6245* (2013.01); *G06Q 2220/10* (2013.01)

(58) Field of Classification Search
None
See application file for complete search history.

(56) References Cited

U.S. PATENT DOCUMENTS 6,546,002 B1  4/2003 Kim
7,590,430 B1  9/2009 Urbanek
(Continued)

*Primary Examiner* — Kevin C. Harper
*Assistant Examiner* — Derrick V Rose
(74) *Attorney, Agent, or Firm* — Patterson + Sheridan, LLP

(57) ABSTRACT

A medical monitoring and surveillance system uses a server communicating with a general-purpose personal device running an application. The application may be downloadable. The application is configured by the server. The application configures the device to perform medical tests using the sensors, preexisting capabilities, and functionality built into the device. The device may be a cellular telephone with data communication and other functionality, a personal digital organizer, a portable entertainment device, or another similar personal device. The application reports the results of the medical tests to the server or a third party device. Various trigger events and associated tasks may be incorporated in the server or in the application residing on the device. A trigger event may occur, for example, in response to the test results meeting one or more predetermined criteria. Once a trigger event occurs, a task associated with the trigger event is performed.

26 Claims, 6 Drawing Sheets

Related U.S. Application Data application No. 61/295,917, filed on Jan. 18, 2010, provisional application No. 61/295,104, filed on Jan. 14, 2010.

(56) References Cited

U.S. PATENT DOCUMENTS

| | | | |
|---|---|---|---|
| 8,225,232 B2* | 7/2012 | Sundararaman | H04M 3/53 715/717 |
| 13,370,428 | 2/2013 | Bayliss et al. | |
| 2001/0013064 A1 | 8/2001 | Cox et al. | |
| 2003/0036683 A1 | 2/2003 | Kehr et al. | |
| 2005/0208925 A1* | 9/2005 | Panasik | H04M 1/72538 455/404.1 |
| 2006/0130150 A1* | 6/2006 | Garza-Gonzalez | G06F 21/31 726/28 |
| 2006/0206590 A1 | 9/2006 | Wakasa et al. | |
| 2007/0100987 A1* | 5/2007 | Aggarwal | G06F 11/3495 709/224 |
| 2008/0270560 A1* | 10/2008 | Tysowski | H04L 51/14 709/207 |
| 2009/0247077 A1* | 10/2009 | Sklovsky | G06F 9/445 455/41.1 |
| 2009/0326980 A1* | 12/2009 | Nolan | G06Q 10/00 705/3 |
| 2010/0049874 A1* | 2/2010 | Chene | G06F 17/30569 709/246 |
| 2010/0286488 A1* | 11/2010 | Cohen | G06F 19/323 600/300 |
| 2010/0321304 A1* | 12/2010 | Rofougaran | G06F 3/046 345/173 |
| 2011/0025611 A1* | 2/2011 | Yoo | A61B 3/0033 345/173 |
| 2012/0164613 A1* | 6/2012 | Jung | G06Q 30/02 434/236 |

* cited by examiner

SYSTEM AND METHOD FOR MEDICAL SURVEILLANCE THROUGH PERSONAL COMMUNICATION DEVICE

CROSS-REFERENCE TO RELATED APPLICATION

This application is a continuation of U.S. patent application Ser. No. 12/906,450 filed Oct. 18, 2010, which claims priority from the following U.S. Provisional Patent Applications: Ser. No. 61/312,943, entitled System and Method for Diagnostics, Monitoring and Surveillance of Individuals Utilizing a Smartphone or Other Remote Device, filed Mar. 11, 2010; Ser. No. 61/348,367, entitled System & Method for Identification and Diagnosis of Tremors, filed May 26, 2010; 61/327,386, entitled System & Method for Movement Disorder Measurement and Quantification, filed Apr. 23, 2010; Ser. No. 61/321,568, entitled A System and Method to Utilize a Smartphone as a Goniometer for Measurement of Range of Movement or Motion, filed Apr. 7, 2010; Ser. No. 61/299,568, entitled Assessing Attention, Fine Motor Skills, Appendicular Coordination, Visual Spatial Processing, Utilizing the Drawing, Writing or Tracing on Interactive Graphics on a Touch Sensitive Screen, filed Jan. 29, 2010; Ser. No. 61/298,077, entitled Visual Acuity, Eye Movement, Color & Contrast Sensitivity Testing Utilizing Interactive Graphics and a Touch Sensitive Screen, filed Jan. 25, 2010; Ser. No. 61/298,068, entitled Visual Acuity, Eye Movement, Color & Contrast Sensitivity Testing Utilizing Interactive Graphics and a Touch Sensitive Screen, filed Jan. 25, 2010; Ser. No. 61/295,917, entitled Reactive Response Test Utilizing Interactive Graphics and a Touch Sensitive Screen, filed Jan. 18, 2010; and Ser. No. 61/295,104, entitled An Invention Measure Fine Motor Speed, Motor Control, and Coordination in the Upper and Lower Extremities Through Interactive Graphics on a Touch Sensitive Screen, filed Jan. 14, 2010. Each of the above referenced patent applications is hereby incorporated by reference in its entirety as if fully set forth herein, including Figures, Tables, Computer Code, and Claims, if present.

FIELD OF THE INVENTION

The present invention relates generally to medical surveillance testing, assessing, and monitoring. In particular aspects, the present invention relates to apparatus, systems, and articles of manufacture for configuring general purpose portable communication devices for medical surveillance testing, assessing, monitoring, and processing information received from such devices.

BACKGROUND

Today's healthcare system is complicated and cumbersome. The processes of testing, diagnosing, monitoring, and performing surveillance of an individual's health are modeled on and reflect old technologies and systems. In many cases, the gathering of diagnostic, monitoring, surveillance and other information occurs through the patient's in-person interactions with another individual, who records, interprets, and saves the information. In other words, the information flows from the patient to an information system indirectly, through an intermediary. There are a number of disadvantages to this approach.

The traditional approach relies on physical proximity of a health care provider (HCP) to the patient. (The concept of health care professional includes, but is not necessarily limited to, medical professionals, such as doctors, physicians, practitioners, chiropractors, dentists, nurses, medical researchers, and medical administrators.) Because many diagnostic tests are performed by an HCP, they require simultaneous physical presence of both the HCP and the patient. The patient thus has to go to the HCP's office or some other location, or the HCP has to come to the patient. This is the so-called Geographic Hindrance.

Moreover, under the traditional approach many tests and evaluations occur in real time, so that the HCP and the patient must be available at the same time. This is the so-called Time Hindrance or restriction.

Even medical services available to patients outside the medical surrounding have generally been restricted to use of custom built medical devices in a client-server model, where the individual accesses a distant server, such as a server hosting a webpage related to the medical service. This limits the patient's ability to access these services to places and times that allow the patient access to the remote server while at the same time having available special purpose medical testing equipment that is acquired for exclusive use in a specific medical function.

Therefore, there is a need in the art to facilitate medical testing, diagnosing, monitoring, and/or performing surveillance of an individual's health. There is also a need in the art to reduce costs associated with medical testing, diagnosing, monitoring, and/or surveillance, and to remove or reduce Geographic Hindrance, physical hardware limitations and/or Time Hindrance.

SUMMARY

Embodiments of the present invention are directed to methods, apparatus, and articles of manufacture that may satisfy one or more of these needs.

In selected aspects, the described embodiments allow a user, such as an individual patient or a patient's caregiver, to self-administer or administer medical test(s); to generate, capture, and provide medical data and/or test results directly into an information system of a healthcare professional, or directly into general-purpose personal device. The general-purpose personal device may be a smartphone, iPad®, iPod®, personal computer (PC), a handheld computer, a personal digital assistant, a cellular telephone, a network appliance, a camera, a smart phone, an enhanced general packet radio service (EGPRS) mobile phone, a network base station, a media player, a navigation device, an email device, a game console, or a combination of any two or more of these data processing devices or other data processing devices. The medical data and/or test results may also go directly into an information system maintained as part of this system, or that of a third party. The results may also remain on the device to be delivered at a physical meeting or appointment. The information may then be analyzed and processed in various ways, providing multiple efficiencies and new models for diagnostics, monitoring, and surveillance.

The need for an intermediary to administer and observe the medical test(s) and then input the results into an information system may thus be eliminated. Moreover, HCP's and the patient's schedules may be decoupled. In contrast to the existing methodology where both parties must be at the same place at the same time, the asynchronous aspect of certain embodiments allows the patient to take a test at an appropriate time and the HCP to review the results at a later time, allowing for remote monitoring and surveillance.

In aspects, the described embodiments enable user-friendly applications to be utilized by the user on a general-purpose personal device, such as a smartphone, iPad®, iPod®, personal computer (PC), a handheld computer, a personal digital assistant, a cellular telephone, a network appliance, a camera, a smart phone, an enhanced general packet radio service (EGPRS) mobile phone, a network base station, a media player, a navigation device, an email device, a game console, or a combination of any two or more of these data processing devices or other data processing devices. The applications may be prescribed by an HCP to the user, and downloaded, pushed, pulled or otherwise transferred to the user's device to configure and enable the device to provide testing, surveillance, and monitoring functions. The applications transform the general-purpose device into a medical device configured to gather information directly from the user, in real time and/or periodically, in the form of surveys and questionnaires, and by enabling tests that the user may perform to create test data and information concerning the user's medical condition or state of wellness. These prescriptive applications extend the medical practitioners reach to the user's device. The ability to integrate the device and communicate with a second device or server enables a two-way means of gathering and delivering data, monitoring the received data, and responding to the data and the test results. The applications need not necessarily prevent other, non-medical uses of the device.

In aspects, the described embodiments provide a means for an HCP to define or identify one or more diagnostic assessments, tests, monitoring protocols, surveillance protocols, and/or other medical applications, to configure or delineate user specific parameters in the applications, and to electronically prescribe the specified applications to one or more users, through remote wireless or direct downloading of prescribed tests, assessments, batteries, diagnostics, surveys, or general data parameter collection applications onto the user's device, such as a handheld smartphone. This allows the HCP to transform the device into a testing, monitoring, surveillance, and diagnostic medical apparatus that can provide the HCP with diagnostic data, diagnostic assessments, and the ability to gather clinical parameters outside the HCP's physical location. Tests can be prescribed for a single point in time, or for specified time lines. Thus, the data can be gathered for a single test, or can be gathered over a time period, for example, over the course of a given disease, treatment, or drug trial.

The described embodiments also allow for the monitoring, surveillance, and testing of groups of individuals for study, clinical trials, and medical supervision. For example, the embodiments may be used for post-marketing surveillance data, such as real-time post-marketing surveillance feedback for pharmaceutical products prescribed to patients in trials. The embodiments may also provide the ability to inform an HCP with response to treatment data that can indicate efficacy or lack of efficacy of a specified medical regimen, and of a need to modify the regimen. The embodiments may remotely capture and send medical diagnostic data to an HCP to indicate response or lack of response to a given treatment. The diagnostic data sent from a user's device and received by an HCP's device or computer can provide valuable time stamped information indicating a need for an adjustment, such as an increase or decrease of dosage for various pharmaceutical products. Data may also be retained and remain accessible at a third party device, the HCP's device, or as part of an integrated information system. The diagnostic data can provide information indicating the need for the user-patient to be seen by a medical professional, for example, to determine whether a change in disease management and treatment is needed. The embodiments can provide tests which indicate the pharmacokinetics and pharmacodynamics of pharmacologic agents.

In aspects, the described embodiments may also incorporate an Application Programming Interface (API) that can be used by third-party application developers to integrate and implement the configurability of a common platform application into other applications built by the developers. The server embodiments described may enable registration and maintenance of third-party applications through the common platform system. The third-party applications may be integrated with the prescriptive and configuration features and abilities of the common platform. The API may be made available to authorized third parties for generating, sending, and accessing data and information gathered by the applications, for integration into other systems and programs. Data access may be provided through automatic importation of the data gathered by the applications into existing information systems utilized by the medical community.

Advantageously, remote capture of diagnostic information of an individual patient may enhance clinical decision-making for disease management.

Advantageously, a device configured to monitor symptoms at shorter intervals than would be economically feasible under the traditional model and obtaining test data in real-time, may also enhance the reliability and accuracy of the information available to HCPs. Efficacy of the treatment programs and/or medication regimens may thus increase. This may be particularly advantageous in for patients with neurodegenerative diseases, who often struggle to have a clear recollection of symptoms that happened over a 4-6 week period between typical doctor's visits.

In embodiments, a method of operating a portable communication device includes these steps: (1) receiving a master configuration file by the portable communication device, the master configuration file including information sufficient for an initialization application to configure each application of one or more applications to execute on the portable communication device for a user of the portable communication device; (2) receiving by the portable communication device the initialization application and said each application of the one or more applications; (3) executing the initialization application by the personal communication device, the step of executing the initialization application including providing for said each application configuration information corresponding to said each application; (4) executing said each application by the portable communication device, the step of executing said each application including said each application reading the application configuration information corresponding to said each application and configuring the portable communication device in accordance with the application configuration information corresponding to said each application.

In aspects, the one or more applications include a first application and a second application; and the first application generates first data used by the second application.

In aspects, the step of providing for said each application configuration information corresponding to said each application includes providing for said each application an application configuration file corresponding to said each application, a different configuration file per application; and the first application includes a medical application.

In aspects, the second application generates second data used by the first application.

In aspects, the method also includes receiving from at least one server first configuration information and second configuration information. The one or more applications include a first application and a second application, the first application generates first data, and the second application generates second data.

In aspects, the method also includes sending to the at least one server a request for the first configuration information and the second configuration information, wherein the step of receiving from the at least one server the first configuration information and the second configuration information is performed in response to the request for the first configuration information and the second configuration information.

In aspects, the first configuration information includes at least one parameter of a diagnostic assessment, test, monitoring protocol, or surveillance protocol, the at least one parameter being specific to the user.

In aspects, the first configuration information includes at least one parameter selected from a group consisting of a diagnostic assessment parameter, a test parameter, a monitoring protocol parameter, and a surveillance protocol parameter.

In aspects, the second application generates, based on interaction provided by the user, data related to condition of the user, timestamps the data related to the condition of the user, and transmits the data related to the condition of the user to at least one remote device when a connection to the at least one remote device is available.

In aspects, the second application generates, based on interaction provided by the user, data related to condition of the user, timestamps the data related to the condition of the user, and transmits the data related to the condition of the user to the at least one server at periodic intervals.

In aspects, the second application generates, based on interaction provided by the user, data related to condition of the user, and transmits the data related to the condition of the user to the at least one server when the data related to the condition becomes available.

In aspects, the second application generates, based on interaction provided by the user, data related to condition of the user, timestamps the data related to the condition of the user, and transmits the data related to the condition of the user to the at least one server.

In aspects, the first application generates, based on interaction provided by the user, data related to condition of the user. The first data includes the data related to the condition of the user, or is generated based on the data related to the condition of the user. The second application causes the portable communication device to modify a regimen of the user in response to the data related to the condition of the user meeting a predefined condition.

In aspects, the second application causes the portable communication device to modify the regimen of the user by displaying regimen modification information to the user.

In aspects, the second application causes the portable communication device to modify the regimen of the user by changing time of an action performed by the portable communication device.

In aspects, the second application causes the portable communication device to modify the regimen of the user by changing time of a reminder provided to the user by the portable communication device.

In aspects, the first application generates, based on interaction provided by the user, data related to condition of the user; the first data includes the data related to the condition of the user, or the first data is generated based on the data related to the condition of the user; and the second application causes the portable communication device to send to the at least one server information related to trigger generation in response to the data related to the condition of the user meeting a predefined condition.

In aspects, the data related to trigger generation includes information related to scheduling of an appointment.

In aspects, the data related to trigger generation includes information related to modification of a regimen.

In aspects, the data related to trigger generation includes information related to scheduling a communication from a provider.

In aspects, the data related to trigger generation includes at least a portion of the data related to the condition of the user.

In aspects, the data related to trigger generation includes at least a portion of the data related to the condition of the user and a request for evaluation of the data related to the condition of the user.

In aspects, the data related to trigger generation includes a request for evaluation of the data related to the condition of the user.

In aspects, the data related to trigger generation includes a request for a third application for the portable communication device, and the method also including receiving, by the portable communication device, the third application in response to the request for the third application.

In aspects, the data related to trigger generation includes a request for a third application for the portable communication device and third configuration information corresponding to the third application, the method also including receiving by the portable communication device, the third application and the third configuration information in response to the request for the third application and the third configuration information.

In aspects, the first configuration information includes a menu option determination for the first application or the second application.

In aspects, the method also includes configuring an external device collocated with the personal communication device based on the first configuration information, the second configuration information, or the first and the second configuration information.

In aspects, the external device and the personal communication device communicate using a short range radio frequency communication standard.

In aspects, the method also includes configuring an external glucose monitoring device collocated with the personal communication device based on the first configuration information, the second configuration information, or the first and the second configuration information.

In aspects, the method also includes configuring an external heart rate monitoring device collocated with the personal communication device based on the first configuration information, the second configuration information, or the first and the second configuration information.

In aspects, the method also includes configuring an external blood pressure monitoring device collocated with the personal communication device based on the first configuration information, the second configuration information, or the first and the second configuration information.

In aspects, the second application generates, based on interaction provided by the user, data related to condition of the user, and the second configuration information configures the personal communication device to prevent, in response to a predetermined condition, the user from seeing at least some test data resulting from the interaction provided by the user.

In aspects, the predetermined condition is based on the data related to the condition of the user.

In aspects, the method also includes receiving by the personal communication device a display flag, wherein the predetermined condition is based on status of the flag.

In aspects, the method also includes receiving by the personal communication device an updated configuration file, re-configuring the personal communication device in accordance with the updated configuration file, the step of re-configuring causing at least one of (1) elimination of a test performed by the first application or the second application, (2) addition of a test to be performed by the first application or the second application, and (3) a change in a test to be performed by the first application or the second application.

In embodiments, a portable communication device includes a first transceiver, a display, an interaction mechanism configured to enable a user of the portable communication device to provide information to the portable communication device, at least one processor, and at least one memory. The at least one memory stores program code executable by the at least one processor. The portable communication device is configured by the at least one processor, under control of the program code, to perform a method with the following steps: (1) receiving a master configuration file, the master configuration file including information sufficient for an initialization application to configure each application of one or more applications to execute on the portable communication device for the user of the portable communication device; (2) receiving the initialization application and said each application of the one or more applications; (3) executing the initialization application, the step of executing the initialization application including providing for said each application configuration information corresponding to said each application; and (4) executing said each application by the portable communication device, the step of executing said each application including said each application reading the application configuration information corresponding to said each application and configuring the portable communication device in accordance with the application configuration information corresponding to said each application.

In aspects, the first transceiver is a cellular telephone transceiver.

In aspects, the step of providing for said each application configuration information corresponding to said each application includes providing, through the first transceiver, for said each application an application configuration file corresponding to said each application, a different configuration file per application; and the steps of receiving the master configuration file, receiving the initialization application and said each application of the one or more applications are performed through the first transceiver.

In aspects, the one or more applications include a first application and a second application; and the method steps also include receiving from at least one server first configuration information and second configuration information.

In aspects, the method steps also include sending to the at least one server a request for the first configuration information and the second configuration information, wherein the step of receiving from the at least one server the first configuration information and the second configuration information is performed in response to the request.

In aspects, the first configuration information includes at least one parameter selected from a group consisting of a diagnostic assessment parameter, a test parameter, a monitoring protocol parameter, and a surveillance protocol parameter.

In aspects, the first application generates first data used by the second application.

In aspects, the second application generates second data used by the first application.

In aspects, the first application generates, based on interaction provided by the user, data related to condition of the user; the first data includes the data related to the condition of the user, or is generated based on the data related to the condition of the user; and the second application causes the portable communication device to modify a regimen of the user in response to the data related to the condition of the user meeting a predefined condition.

In aspects, the first application generates, based on interaction provided by the user, data related to condition of the user; the first data includes the data related to the condition of the user, or is generated based on the data related to the condition of the user; and the second application causes the portable communication device to send to the at least one server information related to trigger generation in response to the data related to the condition of the user meeting a predefined condition.

In aspects, the method steps also include configuring an external device collocated with the personal communication device based on the second configuration information.

In aspects, the portable communication device also includes a radio frequency transceiver for communications using a short range radio frequency communication standard, wherein the external device and the personal communication device communicate through the short range radio frequency transceiver.

In embodiments, a method of configuring a portable communication device includes these steps: (1) sending a master configuration file from at least one server to the portable communication device, the master configuration file including information sufficient for an initialization application to configure each application of one or more applications to execute on the portable communication device for a user of the portable communication device; and (2) sending from the at least one server to the portable communication device the initialization application. When the initialization application is executed by the personal communication device, the personal communication device is provided with configuration information corresponding to said each application, so that the portable communication device is configured in accordance with the application configuration information corresponding to said each application.

In aspects, the one or more applications include a first application and a second application; and the first application generates first data used by the second application.

In aspects, the method also includes sending from the at least one server to the portable communication device an application configuration file corresponding to said each application, a different configuration file per application.

In aspects, at least one of the application configuration files includes at least one parameter selected from a group consisting of a diagnostic assessment parameter, a test parameter, a monitoring protocol parameter, and a surveillance protocol parameter.

In aspects, the at least one parameter is specific to the user.

In embodiments, a portable communication device includes a means for receiving and transmitting, a means for displaying, a means for enabling a user of the portable communication device to provide information to the portable communication device, a means for processing, and a means for storing data. The means for storing data stores program code executable by the means for processing. The portable communication device is configured by the means for processing, under control of the program code, to perform a method including the following steps: (1) receiving a master configuration file, the master configuration file including information sufficient for an initialization application to configure each application of one or more applications to execute on the portable communication device for the user of the portable communication device; (2) receiving the initialization application and said each application of the one or more applications; (3) executing the initialization application, the step of executing the initialization application including providing for said each application configuration information corresponding to said each application; and (4) executing said each application by the portable communication device, the step of executing said each application including said each application reading the application configuration information corresponding to said each application and configuring the portable communication device in accordance with the application configuration information corresponding to said each application.

In embodiments, at least one memory device stores computer readable code for performing steps of a method of operating a portable communication device. The method includes (1) receiving a master configuration file by the portable communication device, the master configuration file including information sufficient for an initialization application to configure each application of one or more applications to execute on the portable communication device for a user of the portable communication device; (2) receiving by the portable communication device the initialization application and said each application of the one or more applications; (3) executing the initialization application by the personal communication device, the step of executing the initialization application including providing for said each application configuration information corresponding to said each application; and (4) executing said each application by the portable communication device, the step of executing said each application including said each application reading the application configuration information corresponding to said each application and configuring the portable communication device in accordance with the application configuration information corresponding to said each application.

These and other features and aspects of the present invention will be better understood with reference to the following description, drawings, and appended claims.

DETAILED DESCRIPTION

Figure 1:
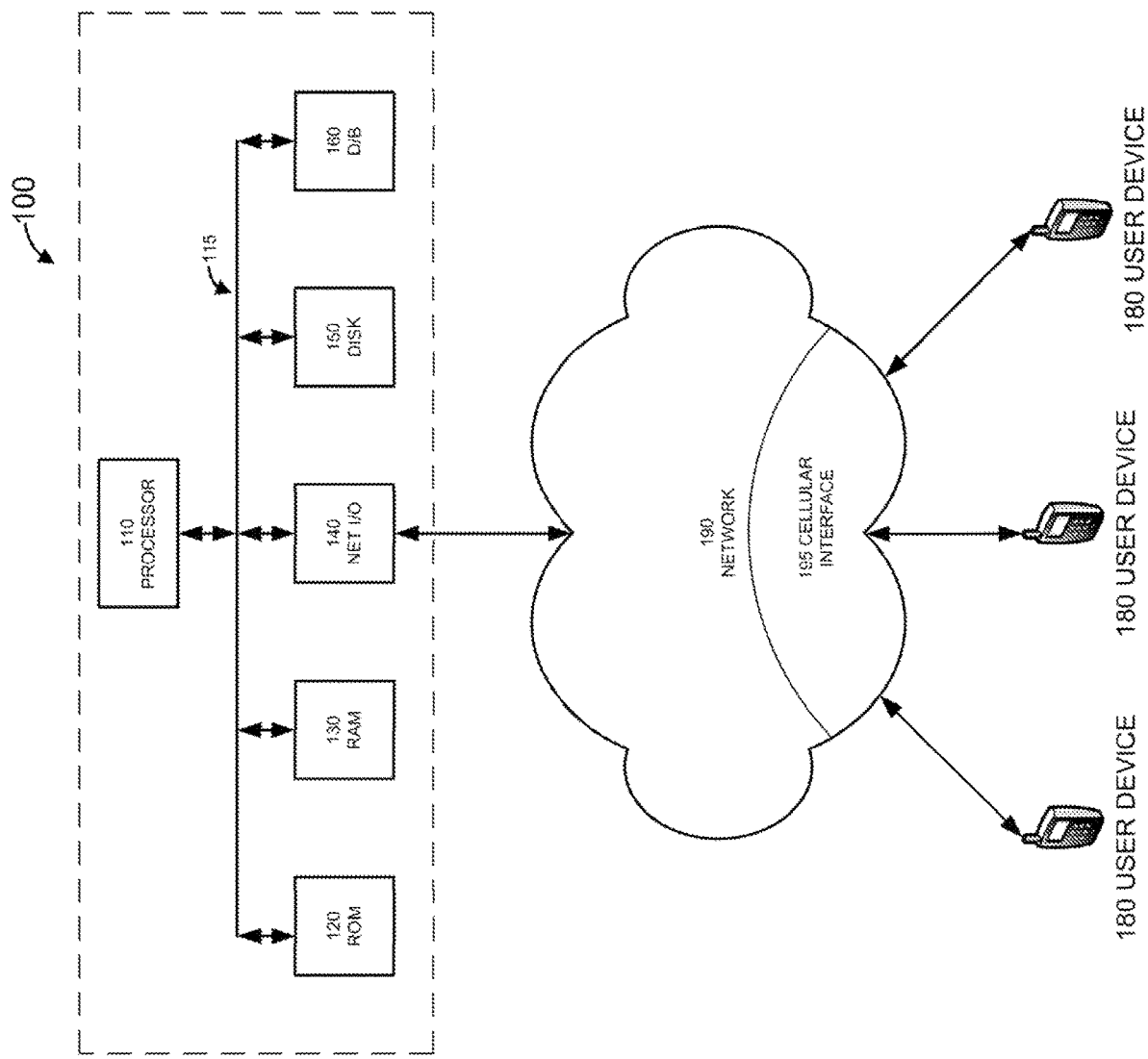
FIG. 1 illustrates selected components of a server configured to perform in accordance with selected aspects of the present description.

In this document, the words "embodiment," "variant," and "example" refer to particular apparatus, process, or article of manufacture, and not necessarily to the same apparatus, process, or article of manufacture. Thus, "one embodiment" (or a similar expression) used in one place or context can refer to a particular apparatus, process, or article of manufacture; the same or a similar expression in a different place can refer to a different apparatus, process, or article of manufacture. The expression "alternative embodiment" and similar expressions and phrases are used to indicate one of a number of different possible embodiments. The number of possible embodiments is not necessarily limited to two or any other quantity. Characterization of an item as "exemplary" means that the item is used as an example. Such characterization of an embodiment does not necessarily mean that the embodiment is a preferred embodiment; the embodiment may but need not be a currently preferred embodiment. All embodiments are described for illustration purposes and are not necessarily strictly limiting.

The words "couple," "connect," and similar expressions with their inflectional morphemes do not necessarily import an immediate or direct connection, but include connections through mediate elements within their meaning.

The expression "medical application" refers to a software application (such as an iPhone® application and analogous applications for competing platforms) for performing or facilitating at least some part of a medical or health-related diagnostic assessment, medical or health-related test, medical or health-oriented monitoring protocol, medical or health-related surveillance protocol, and similar activities related to provision of healthcare and health maintenance services to a user of the application, or to another person. Medical applications may relate to drug testing and other similar activities that may or may not benefit directly the person tested, diagnosed, monitored, or subjected to surveillance. The term "application" includes within its meaning "medical application." It also extends to applications that are not strictly speaking "medical" in nature, although it may integrate with one or more medical applications to achieve some health-related benefit. For example, a software application for monitoring a person's blood pressure or serum glucose level would be both an "application" and a "medical application" as defined herein. A software application for monitoring running performance—speed, distance, calorie burn rate—is an example of an "application," but not of a "medical application."

The word "interaction" and its inflectional morphemes, when used in the context of a user's intercourse with a portable communication device or applications executing on such device, relate to providing information to the device or application(s). The information may be "input" into the device or application by providing it directly in the form of input through means designed for the user to provide input defined data, such as a keyboard, touchpad, touch sensitive screen, or microphone. An interaction subsumes input of information, and additionally includes provision of information through a sensor not intended for information input by the user, such as a vibration sensor, a temperature sensor, and a medical sensor (a glucose sensor, blood pressure sensor, heart rate monitor, etc.).

When used in relation to "applications," the word "configure" and its inflectional morphemes signify setting up a particular application for performing its intended function on a specific operating platform of a personal communication device (including both hardware and software components of such platform). The word "configure" and its inflectional morphemes, when used in relation to multiple applications, also refer to interrelating the various elements of these multiple applications to facilitate some end result of the use of these multiple applications. Interrelating may include affecting not just the multiple applications, but also setting up the hardware/software components of the operating platform and, if applicable, to the hardware/software components of external device(s) intended to be plugged into the operating platform or otherwise connected to the operating platform via short-range means (as discussed below) for functioning with an application.

Other and further definitions and clarifications of definitions, both explicit and implicit, may be found throughout this document.

Reference will now be made in detail to one or more embodiments selected aspects of which are illustrated in the accompanying drawings. Same reference numerals may be used in the drawings and the description to refer to the same apparatus elements and method steps. The drawings are in a simplified form, not to scale, and omit apparatus elements and method steps and decisions that can be added to the described systems and methods, while possibly including certain optional elements, steps, and decisions.

FIG. 1 is a simplified block diagram representation of a computer-based system 100 configured in accordance with selected aspects described herein. As shown in FIG. 1, the system 100 is coupled to portable user devices 180 via a communication network 190. FIG. 1 does not show many hardware and software modules of the system 100, and omits several physical and logical connections. The system 100 can be implemented as a special purpose data processor, a general-purpose computer, a computer system, or a group of networked computers or computer systems configured to perform the steps of methods described below. In some embodiments, the system 100 is built on a personal computer platform, such as a Wintel PC, Linux, Unix, or a Mac computer. The personal computer may be a desktop or a notebook computer. In other selected embodiments, the system is a dedicated or a non-dedicated server configured to perform the method steps described in this document.

The exemplary system 100 includes a processor 110, read only memory (ROM) module 120, random access memory (RAM) module 130, network interface 140, a mass storage device 150, and a database 160. These components are coupled together by a bus 115. In the illustrated embodiment, the processor 110 is a microprocessor, and the mass storage device 150 is a magnetic disk drive. The mass storage device 150 and each of the memory modules 120 and 130 are connected to the processor 110 to allow the processor 110 to write data into and read data from these storage and memory devices. The network interface 140 couples the processor 110 to the network 190, for example, the Internet. The nature of the network 190 and of the devices that may be interposed between the system 100 and the network 190 determine the kind of network interface 140 used in the system 100. In some embodiments, for example, the network interface 140 is an Ethernet interface that connects the system 100 to a local area network, which, in turn, connects to the Internet. A cellular interface 195 provides a connection between the network 190 and the user devices 180. As noted above, the user devices 180 may include smartphones, iPads®, iPods®, PCs, and PDAs.

The database 160 is used for organizing and storing data that may be needed or desired in performing the method steps described in this document, including storing the test data obtained from the user devices 180. The database 160 may be a physically separate system coupled to the processor 110, as illustrated in FIG. 1. In one alternative embodiment, the processor 110 and the mass storage device 150 are configured to perform the functions of the database 160.

The processor 110 reads and executes program code instructions stored in the ROM module 120, the RAM module 130, and/or the mass storage device 150. Under control of the program code, the processor 110 configures the system 100 to perform the steps of the described methods. In addition to the modules 120/13 and the storage 150, the program code instructions may be embodied in machine-readable storage media, such as hard drives, floppy diskettes, CD-ROMs, DVDs, and similar devices. The program code can also be transmitted over a transmission medium, for example, over electrical wiring or cabling, through optical fiber, wirelessly, or by any other form of physical transmission. The transmission can take place over a dedicated link between telecommunication devices, or through a wide- or local-area network, such as the Internet, an intranet, extranet, or any other kind of public or private network. In one embodiment, the program code is downloaded to the system 100 through the network interface 140.

Figure 2:
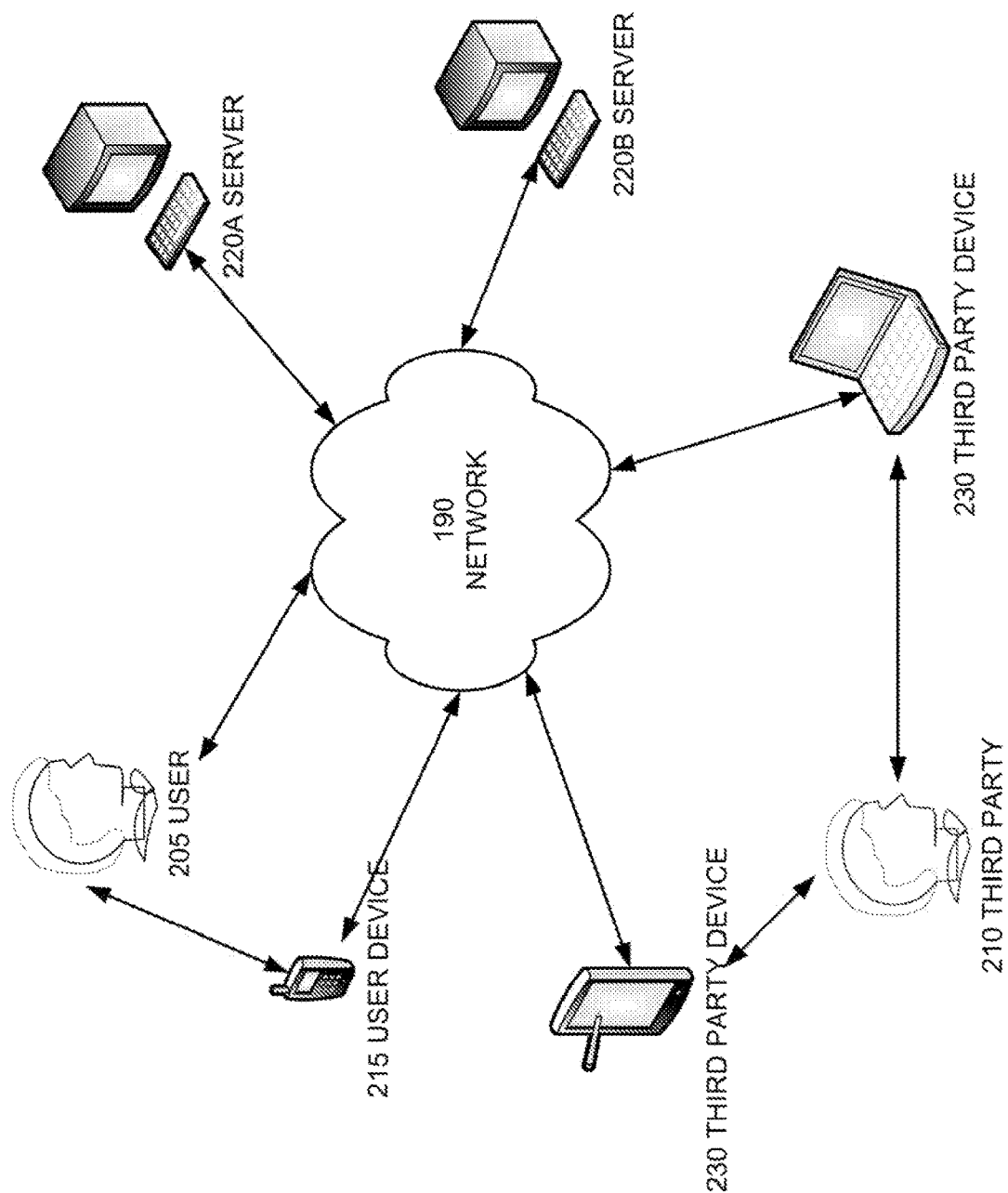
FIGS. 2 and 3 are simplified representations of selected aspects of communications between a user at a user device running an application and another party.

FIG. 2 is a simplified representation of selected aspects of communications and information transfer between a user 205, another party or administrator 210, and servers 220A/B. The administrator 210 may be, for example, an HCP, a teacher, an organization such as an educational institution, a public health system, a research institution, and a law enforcement agency. The user 205 may be a patient, a caregiver of a patient, or another individual. The administrator 210 may prescribe the use of an application to the user 205, to gather data. The user 205 may use a device 215 (such as the device 180 of FIG. 1) on which the application can be run, to access the servers 220A and 220B through the network 190. Note that the two servers 220 may be identical or different; note further that only one of the servers may be used, and therefore the description below will refer generically to the server 220. (A third party device 230 may also be used as a server.) The server 220 may be implemented as the system 100 shown in FIG. 1. The user 205 may download and install the application on the device 215. The user may download the application from the server 220 or another source, such as the Apple App Store. The application may be pushed to the user's device via a connection to the server, or pulled by an existing program, application, action, or event. The latter may include a link in an email, sms, or other electronic communication to the device, a trigger action or result with an existing application or function on the device.

The administrator 210 may prescribe the application to the user 205 in various ways, including through the server 220 or another device such as a personal computer. The administrator may also provide to the user 205 the device 215 pre-configured with the prescribed application or applications. Alternatively, the user 205 may download and install the application on the device 215 and then register with the administrator 210 through the server 220. The registration may be automatic, triggered by the installation of the application on the user's device 215, or may take place by the user's providing/inputting the required information to the application. The registration may be in the form of e-mail, text, voice mail, a webpage form, or some other means of communication, electronic or otherwise.

The user's information input into the application that may trigger an automatic communication to the administrator 210 may include a specific identification code that affects another device, or information that allows the application to communicate directly with the HCP, for example, by automatically generating an email message or other communication to the HCP's e-mail address or device. The application may also configure the user's device 215 to send automatically the collected information to the administrator 210, a third party, a server, or another device at one or more predetermined times or after a predetermined time interval.

Figure 3:
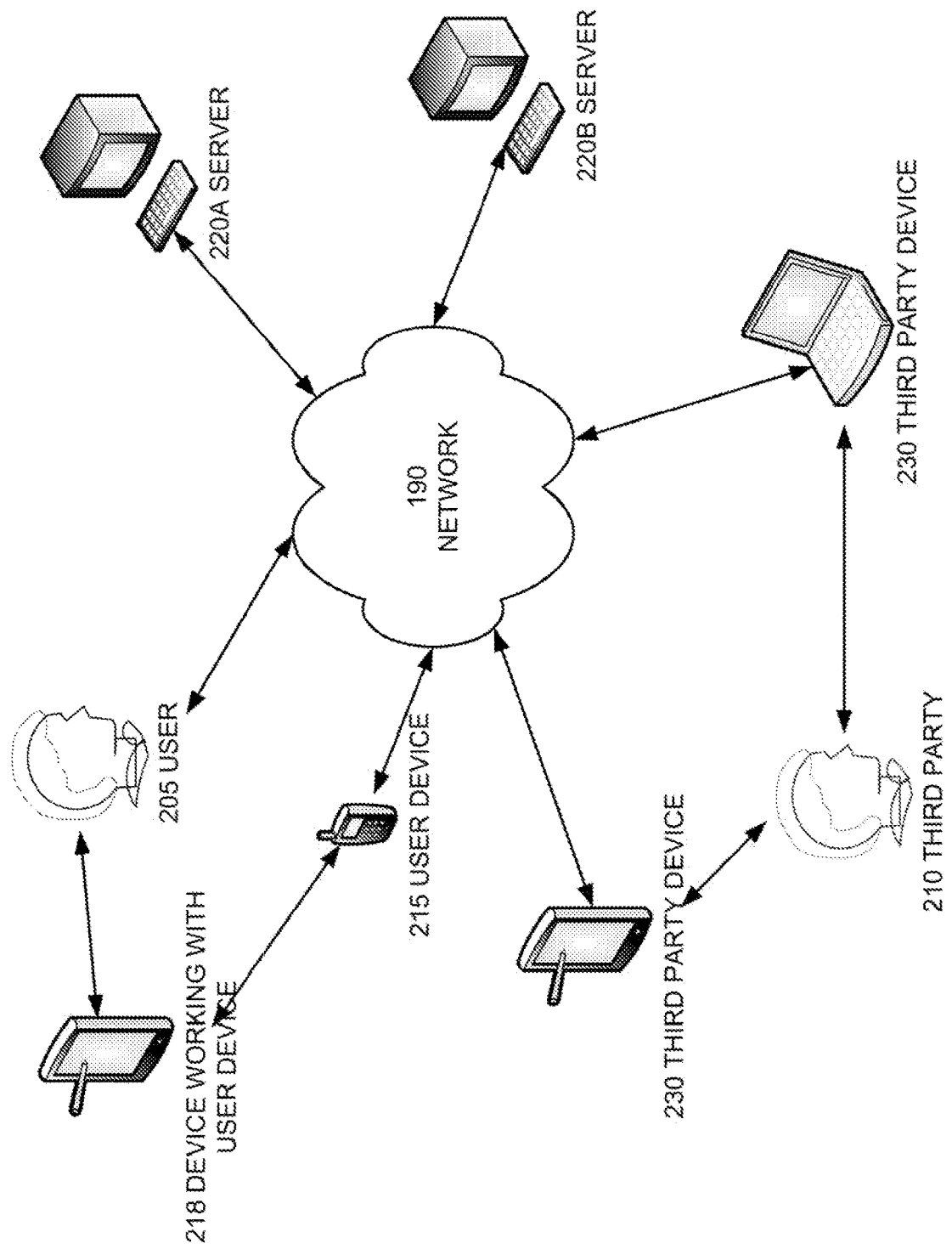

FIG. 3 is another simplified representation of selected aspects of communications and information transfer between the user 205, another party or administrator 210, and the server 220. The communications shown in FIG. 3 are generally similar to those shown in FIG. 2, with the difference being that the user's device 215 now communicates with another device 218 co-located with the user's device 215. The device 218 may be plugged into the device 215; connected to the device 215 through a short cable, say less than four feet in length; or configured to communicate with the device 215 using a communication standard (such as Bluetooth™) that operates over short distances, which may be, for example, 10 meters or less, and 1 meter or less. In embodiments, the device 218 may be implanted into a person's body. The device 218 may be a dedicated device designed to facilitate the gathering of the user's medical information. For example, the device 218 may be a blood pressure gauge, a heart rate monitor, or a glucose monitor. The device 218 may be attached to the user's device 215, so that both portable devices can be carried together. The device 218 may be configured to communicate with the user device 215, and through the user's device 215 and the network 190 with the server 220 or another remote device. The user's device 215 may receive data from the device 218, and may provide the device 218 with software and configuration data, so that the device 218 may be configured by the user 205 or by a remote device such as the server 220.

The application may employ a configuration file containing configuration information that determines functional, aesthetic, and/or other parameters of operation of the user device 215, under control of the application. The configuration file may be an eXtended Markup Language (XML) formatted file. The configuration information for the user device 215 and the application is not limited to this form. The configuration file may be stored by various means, including text files stored in databases such as a DataStore database. The configuration file may include one or more settings, each setting being a key-value pair. Upon initial installation or at a later startup of the application, the application may read or import the data found in the configuration file. The configuration file may be accessed and/or downloaded every time the application starts-up, periodically, in response to updates of the configuration file or data, in response to selection of a new or additional configuration file, in response to an action or result occurring with or from the application or other application or source, or in response to downloading of a new configuration file.

Figure 4:
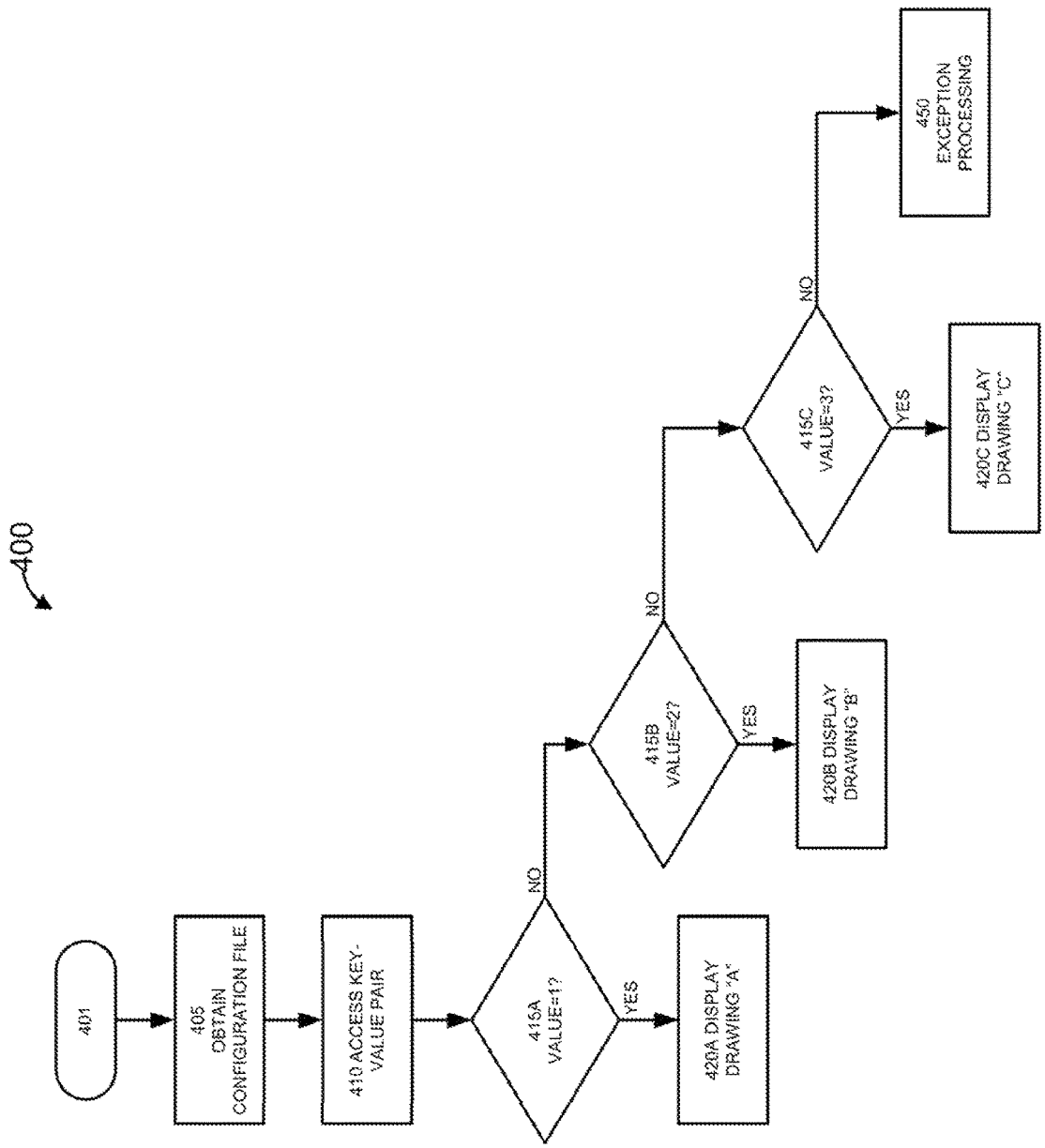
FIG. 4 is a process flow diagram illustrating selected steps and decision blocks of configuring an application on a user device.

FIG. 4 is a process flow diagram illustrating selected steps and decision blocks of a process 400 for configuring the application and the user device 215 based on a key-value pair in the configuration file. At flow point 401, the application is executing on the user device 215. At step 405, the application reads the configuration file; for example, the application reads the configuration file from memory or other storage of the device 215 or connected to the device 215, or the application downloads the configuration file from the server 220 or another source, such as a Bluetooth, wifi, or hard wire connection, or through a means such as a cellular network or the Internet. At step 410, a configuration process of the application accesses a given key-value pair of the configuration file. In decision blocks 415A, 415B, and 415C, the application selects a particular step in which the application and/or the user device 215 is (or are, as the case may be) configured according to the specific value of the given key-value pair. Thus, step 420A is performed in response to the key-value pair being a value_1, step 420B is performed in response to the key-value pair being a value_2, and step 420C is performed in response to the key-value pair being a value_3. If the key-value is not equal to any of the predefined values, an exception (error) is processed in step 450.

In the example shown in FIG. 4, the configuration file is used to modify a menu option within the application. Here, the application reads the configuration file (step 405), and the configuration process determines (step 410) how a menu item will function based upon a variable (the key-value pair) in the configuration file. The configuration file may include key-value pairs that are identification and data match pairs; an identifying label or data is matched with the data or variable itself. The configuration file may also store variables in a predetermined order, or variables may be stored and identified in predefined records. This allows the application to search the configuration file for the existence of a particular variable. The application may be programmed with a default selection if no variable is present. The configuration variable may allow the application multiple alternatives; three alternatives are shown in FIG. 3, but a smaller or greater number of alternatives may be available. Once the configuration file has been read and the variable accessed, the application can present the menu item as a functional button. The button may be visible and functional; and visible but grayed out, indicating an inactive alternative. Moreover, the menu item and its corresponding button may be entirely eliminated.

The configuration file may contain one or more variables that determine (set) type font and type size for all or some of the elements displayed by the user device 215. Other type characteristics may also be determined by a variable in the configuration file, for example, italicization, bolding, and color. The configuration file may also contain a variable setting the language of the displayed text, including menu items, labels, and instructions.

The configuration file may contain one or more variables that determine if particular test results are displayed. A variable in the configuration file may allow the user to view one or more current results and/or a variable number of past result(s). In variants, a variable in the configuration file may determine that specific results are to be concealed from the user, either by default or as a function of the specific result value and/or external variable(s). For example, a variable in the configuration file may conceal results (current and/or past) if the application does not receive authorization to display the results from the server 220. The server 220 may be configured to block automatically the display of the test results on the user device 215 if a condition is or is not satisfied, for example, if the user has not seen the HCP within a predetermined period, if payment has not been received, or if test results fall in a range that is predetermined as potentially upsetting to the user. The server 220 may control display of the test results by granting or denying authorization in response to an automatic request that the user device 215 sends in accordance with a variable in the configuration file. The server 220 may also control the display of the test results by modifying the configuration file so that at the application's current session or next start-up the application reads the variable determining the test results display is set not to allow display of selected test results or of all the test results.

In embodiments, the server 220 uses the configuration file to vary (add, delete, and/or change) machine-executable instructions (i.e., computer code) of the application. The configuration file may include variable(s) determining the specific versions of the instructions, or contain links to different versions of the user instructions that can be automatically downloaded and integrated into the application. Varying the instructions through a mechanism provided by the server 220 (i.e., the configuration file) may enable changes in the configuration of the application, for example, addition or elimination of a test or a test option. Varying the instructions through the server-provided mechanism may also enable making changes in the intended way the application is to be used, for example, a measurement of one kind of movement (e.g., of a stylus or finger on a touch-sensitive screen of the device 215) versus another kind of movement, or to address individual user preferences or considerations such as the user's medical condition. For example, the user may be asked to trace various predetermined figures (straight lines, circles), so that the resulting traced pattern can be compared to the predetermined figure shown on the screen of the device 215. Furthermore, varying the instructions through the server-provided mechanism may enable changes to address environmental or other external factors, such as the user's involvement with a specific group, the user's association with a specific medical professional study, or other externally-determined parameters.

In an embodiment, the application may allow the user to select a configuration file, or the application may access a default configuration file. The configuration file(s) utilized by the application may be stored on the user device 215 or may have been included with the application itself. The application may access configuration files stored remotely (e.g., the server 220 being accessed by the user device 215). The existing configuration file(s) may be updated or replaced with alternative file(s) that may be located on the user device 215 or remotely. In an embodiment, the user device 215 may access the remote configuration file(s) over the Internet. In embodiments, the application may access the server utilizing a "URL Fetch" to issue HTTP and HTTPS requests, and to receive responses. The URL fetch may return a list of available configurations to the application from which the user 205 may select the desired configuration file, or the application may automatically selects a configuration file based upon preset parameters, such as the most recently created configuration file.

In embodiments, the user 205 may be able to input into the application an identification code corresponding to a particular configuration file, so that that the application can identify the configuration file to use in response to the user's input. The user may also be able to input an identification code that is entered in a link or embedded code sent to the device. The link or embedded code may initiate the download of an application in turn inserting the configuration code, or call and start an existing application and inserting a configuration code. The application may use multiple configuration files with multiple configuration sets, either concurrently or alternatively. For example, one of the configuration files may be used to provide data on a certain set of application options, such as options expressing user preferences (language, font style, font size, and other language-related parameters). Additional configuration file(s) may provide variables for other aspects of the application's functionality and operations, such as restrictions imposed on the viewing of test results, lengths of tests, availability of menu items, availability of user configuration, and other parameters.

In embodiments, all configuration settings for a particular application and/or a specific configuration version may be compiled in the form of XML or other electronic format at the server 220. Using a communication method such as URL Fetch, the application may make a request ("http://<Server address>/config/list") with parameters "secretkey—the Configuration key" and receives as a response a configuration file, which is handled by the API of the user device 215.

In embodiments, multiple configuration files for the same application are available on the device 215, to accommodate multiple users of the device 215. Any of the users can select his or her name or other identification from a list, and, in response, the device 215 under control of the application code would then identify the corresponding configuration file(s) and configure itself and/or the application accordingly, for the particular user. In the list of users and user configurations, the application may also include default configuration file(s). The application may have multiple configuration files that reflect certain types, groups, or other parameters. The application may include a list of configuration files that are linked to specific medical conditions, such as Parkinson's or multiple sclerosis (MS), or demographic categories, such as gender, dominant hand, age, and similar categories. The application can then configure the device 215 to offer to the user the linked selections, without reference to the identity of the user.

In embodiments, the configuration file may contain one or more variables determining various test parameters of the application. These parameters may include the time provided for a test, variations in the test, items or parameters to be tested, whether the results are to be displayed to the user, and other parameters. In embodiments, there may be multiple tests or multiple combinations of the tests for which a configuration file may enable or limit accessibility, functionality, and implementation by the user.

In embodiments, the configuration file may contain information identifying a person or an entity that created it, date of its creation, identity of application(s) for which it is intended, a date range of validity of the configuration file (outside of which range it may be automatically prevented from being used to configure the device 215), an implementation date, a version or series identification, and/or other information.

In embodiments, there may be an "Initialization Application" intended to implement a prescription of applications and their corresponding configuration files. The Initialization Application is configured to access a master configuration file that identifies additional applications (i.e., applications in addition to the Initialization Application) and configuration file(s) to be utilized with the additional applications. The Initialization Application may be an independent application or a feature or function previously incorporated in the device. Utilizing this information, the Initialization Application may enable the device 215 to download and install the additional applications identified in the master configuration file. In turn, each of the additional applications downloaded and installed uses configuration file(s) identified in the master configuration file as corresponding to the additional application. The administrator 210 can identify the tests, surveys, and applications for the user or a group of users. The administrator 210 can also identify or create specific configuration files for each of these additional applications. This information can be compiled into a master configuration file with a unique identification. The administrator can then prescribe to the user 205 a single application to install, which in turn will allow a single piece of identification to be placed within this application, providing the Initialization Application with the information and identification of the master configuration file.

In embodiments, the user 205 may be presented with the list of applications that the Initialization Application intends to place on the user's device 215 and the applications' respective configuration file(s). The user 205 may be given the ability to allow the Initialization Application to install these applications and configuration file(s), as the user selects. The user 205 may be able to view detailed information about each application and its corresponding configuration file(s) before deciding whether to authorize installation. This detailed information may be contained within the master configuration file, the individual configuration file(s), or provided through another source. The information may also be contained in the Initialization Application. The party creating the master configuration file may select which steps are visible to the user and what information is presented to the user, and what degree of control and monitoring the user has over the application installation process and its various steps.

In embodiments, the Initialization Application may allow the user 205 to input into the device 215 and/or the server 220 information about the user 205, including demographic data, survey responses, and other factors. To input the data, the Initialization Application may present the user 205 a survey or series of questions, the responses to which the Initialization Application can then use to determine the proper master configuration file and/or individual applications and additional configuration file(s) corresponding to the additional applications that would be appropriate for the specific user 205. In variants, the input of the user 205 is limited to an identification code that indicates other data related to the user, such as the user's doctor or other HCP, the user's medical condition(s), and/or demographic data; in other variants, the user 205 is enabled to enter other information that the Initialization Application can use to determine (create and/or edit) the master configuration file. In variants, the Initialization Application configures the device 215 to present a series of questions and results to suggest or guide the user to the proper additional applications for the user's needs or objectives, and the corresponding configuration file(s) for those additional applications. The Initialization Application may then select the appropriate applications and configuration file(s) based on the user-provided information.

In embodiments, the configuration file(s) may be digitally signed or encrypted using public key encryption or other form of encryption. Encryption is useful to identify and verify the identity of the creator of the configuration file(s), and prevent modification by unauthorized parties. The applications corresponding to the encrypted files may contain encryption keys, or be otherwise enabled to obtain the keys, so that the configuration files can be decrypted.

After the user 205 installs an application (which may be an Initialization Application or another application) on the device 215, the application may configure the device 215 to enable the user 205 to discover configuration file(s) appropriate for the user 205, for example, configuration file(s) appropriate to the user within guidelines provided by a third party, such as the administrator 210. The third party may also configure the application that is installed on the device 215, through the use of the configuration file or otherwise. The ability to change or modify an existing configuration may be limited to changes in specific data items, restricted to preauthorized entities, or made entirely unavailable to the user 205. The server 220 may provide the user 205 with the ability to configure the application by providing the user a code or a password unlocking this feature, fully or in part.

The third-party 210 may send, cause the user's device 215 to transfer (download), or otherwise place configuration file(s) on the user's device 215, to be used with one or more applications of the device 215. The user 205 may also be able to access remote configuration file(s) to be utilized with one or more applications, before downloading the file(s). An application itself may access remote configuration file(s) and configuration file(s) already on the device 215, to modify configuration of itself or of other applications on the device 215.

The third-party 210 may also access the server 220 to create configuration file(s). The third-party may access the server 220 through the Internet, for example, using an application on the third party's device 230 that communicates and interrelates with the server 220. (Two third party devices are shown, but one such device or more than two such devices may be used in embodiments.) The third party 210 or the user 205 may build, modify, and/or update a configuration file for one or more applications of the user device 215, including the master configuration file to be used by the Initialization Application of the user device 215.

The party accessing the server 220 (e.g., the user 205 or the third party 210) may select from a list of existing applications, or define a new application to be used with the device 215 and the server 220. With an existing application, the configuring party may access any default configuration files containing default parameters, modify or leave unmodified the default application configuration file, and provide a unique identification for the configuration file(s). Each application may have associated with it one or a series of keys that identify unique configurable options in that application. Each key may be associated with an instruction, data to provide instruction, logic, or some other trigger to configure the application. The configuring party may create a configuration file for a single user, a predetermined group of users, or a specific type of users. The configuration file creator may limit access to the configuration file to specific individuals or groups. The participating users or groups of users may be provided with data to identify the configuration files and authorization means (e.g., codes, passwords) to access those files and install them with applications on their devices 215.

The configuring party may access the server 220 to enable a new or updated application to use configuration file(s) associated with the new application. The configuring party may create a unique identification for the application, and define the keys (of the key-value pairs) that are available for configuring the application. The configuring party may define the values that may be associated with a particular key. Value definitions may be by a value range, value types, specific values, or other parameters that may be associated with those identifying keys. The party creating the setup for access to a new or a modified application may be restricted, and use of predetermined keys or certain configuration abilities by other parties may be limited.

In embodiments, the application may be configured to define what data may be obtained from the application, what parties may access the data, how much of the data is available to various parties, how the data may be stored, and how the data may be sent to a remote location or retrieved from a remote location. The application may have a series of menus and screens that allow the user 205 or the third-party 210 to configure the generation, collection, management, distribution, and use of the data created and/or gathered by the application. The application may also use configuration file(s) to set, modify, and update these parameters. Configuration settings for the data gathered by the application may include the amount of data collected, the number of results, what data may be accessed by the user 205 or by the third party 210, what data may be shared with other parties, and the manner in which the data is made available (e.g., textual, graphic). The data may remain on the device 215 and may be accessed directly by the user 205 or the third-party 210 from the device 215. The data may be sent or pulled (uploaded) to a remote location such as the server 220, where it may be made available to the user 205, the third party 210, or to other parties. The data may be sent under various conditions defined by the application and/or the application's configuration file(s). For example, the data may be sent every time new data is created, periodically, after a certain number of data gathering points, or in response to some other condition provided from the application side. The data may be pulled by a device at the remote location after the user device 215 has contacted the device at the remote location, or after the device at the remote location contacts the user device 215. The data may be stored in an encrypted format and may be transferred through encrypted means.

In embodiments, the applications may be configured to transfer or send the gathered data to multiple servers, e.g., the servers 220A and 220B. One of the multiple servers 220 may include systems such as an individual user health data vault, and third-party data storage systems. The data collected from the application may also be sent to the server 220A, and then automatically (or in response to satisfaction of predetermined conditions) forwarded from the server 220A to the server 220B.

More generally, one of the servers 220 may be configured as a store and forward device, for forwarding to any kind of entities. The application can also send the data directly to another device, database, or another application on the same device 215 or on another user device. The application may send the data to the server identified in the instructions of the application. The instructions for data delivery may reside on the server 220.

In embodiments, one server (e.g., 220A) may act as the configuration file server, while a second server (e.g., 220B) may act independently or in conjunction to accept, transmit, and/or store data generated by the applications or for the applications of the user device 215.

In embodiments, an application's configuration file(s) may be changed, updated, or otherwise modified based upon data gathered or produced by the application or another application. A configuration file or multiple configuration files may set parameters in the application for the modification of configuration file(s). Parameters may be set on the server which, upon receiving data triggering a predetermined parameter, would in response initiate a change in the configuration file, or the replacement of an existing configuration file with a new configuration file.

The third party 210 may configure an application to survey and gather data directly through the user's input. The configuration file may define one or more questions for presenting to the user 205. The user's responses or other feedback may be sent to the third party 210. The application can be configured to implement this dynamic form of data gathering by combining two sets of key values. The first set may define one or more questions, and the second may capture the user's response or responses. Multiple sets of questions can be generated within the configuration file. The survey may be initiated by the user 205, may be triggered by test results obtained from the device 215, or may be responsive to other interactions of the user 205 with the application or other applications. The survey may also be performed at predefined times, and/or periodically. The data type captured from the user may include the following:

The choices of the user 205 from a list of multiple choice responses (multiple choice);
Yes/no or true/false answers given by the user 205 in responses to questions (binary);
Entries of a number value made by the user 205 (numeric);
The choice of a number within a specific range, such as a pain scale rating, made by the user 205 (range-based);
Alphanumeric responses entered by the user 205, such as a description, a phrase, or a word (textual); and
Audio and video responses recorded by the user 205 (audio/verbal, video/visual).

In embodiments, the application enables monitoring and surveillance of the user 205 by the third-party 210, which may be combined with automated means of gathering, monitoring, and evaluating data generated by the application and or other applications.

The features of the various embodiments described above may be implemented through use of one or more trigger events on the server 220, which can be established by the user 205 or the third-party 210. For example, when the user 205 activates assessment of a medical condition using an application on the device 215, the diagnostic data yielded from the assessment is sent via a wireless network to the third party 210, directly or through the server 220. The server 220 (which receives the diagnostic data directly, from the third party 210, or from the third party device 230) is configured to compare the diagnostic data to predetermined triggering values (i.e., triggers), which may have been established by the third party 210. In variants, the server 220 transmits the data to the third party 210 in response to some datum being equal to a trigger, exceeding a trigger, or being less than a trigger; more generally, the data is transmitted from the server 220 to the third party 210 in response to at least a portion of the data (e.g., some baseline or normative datum/data of the user 205) being in a predetermined relationship with at least one of the triggering values. The server 220 then sends an alert signal to the third party 210. The alert may include biological data of the user 205$m$ such as the test data. A decision rule engine configured in the server 220 and/or another device of the third party 210 analyzes the data and decides whether to send a message to the user 205 and the content of the message. The server 220 may be configured to bill and invoice a fee for using the system and processing the alert.

In embodiments, the server 220 enables a party (e.g., the user 220, the third party 210, or yet another party) to schedule one or more trigger events to run manually or automatically at a specified time or date. A trigger event is a program or a set of logic constraints in a search that may cause a task to be performed using the information on the server 220, or in the application on the user device 215. Trigger events may occur at a single predetermined time, periodically, or at scheduled times. Each trigger event is paired with a corresponding trigger task, which performs one or more specific tasks or functions as defined by the users and other parties (e.g., the user 205 and the third party 210). A trigger task may run every time its corresponding trigger event occurs, or its operation may be dependent upon specific data results related to the trigger event. Predefined tasks may be selected and scheduled by a party to analyze, utilize, or in some other way interface with the data on the server 220 or in the application on the user device 215. A task may include searching, filtering, or some other evaluation or utilization of data that, if meeting certain parameters, triggers a subsequent (different) task. By accessing the server 220 through the web interface, the user 205 or the third party 210 may select from a predefined set of trigger events and build new trigger events. A trigger event may include the following indications obtained through searching of the data from applications on the device 215:

An indication that the user 205 has failed to use a particular application (or particular applications, or test(s) of particular applications) within a specified time;

An indication that the user 205 has used a particular application (or particular applications, or test(s) of particular application(s)) within a specified time;

An indication that an application's configuration (e.g., configuration file) has been changed;

An indication that the results from an application are above, below, or within a set of parameters; and An indication that a specific number of data points collected by an application has been reached.

A triggering task may be paired with an action task. The server 220 and/or the device 215 can then initiate an action task in response to predetermined parameters being met or not met. An action task may include, for example, code for performing notifications and other actions, including these:

Notification of a party (e.g., the user 205 and/or the third party 210) in response to change(s) in an application's configuration;

Notification of a party if one or more predetermined results from an application are above a predetermined threshold, below a predetermined threshold, within a predetermined range, or otherwise meet(s) one or more predetermined criteria;

Notification in response to reaching a specific number of data points for an application, for example, reaching a predetermined number of test measurements obtained within a set period or after a given point in time;

E-mail or text notification of the third party 210 or another entity with results of a search of the data collected by an application;

E-mail or text notification of the third party 210 or another entity with the summary of data collected by an application;

Notification of the third party 210 or another entity that the results from an application fall below a predetermined range threshold, above a predetermined range threshold, within a predetermined range, or outside a predetermined range;

Provision of additional or follow-up information to the user 205 if certain trigger parameters are met or not met; and Notification of the third-party 210 or another entity that a trigger event has occurred.

In embodiments, a party (the user 205, the third party 210, or another entity) may access the server 220 to create or modify a unique trigger event, trigger task, and/or action task. The party may also schedule a task through a web interface or an application interfacing with the server 220. A trigger or action task may include searching, exporting, analyzing, or some other way of utilizing data collected by application(s). A link may be defined to initiate an action task if the trigger task delivered results meeting predetermined criteria.

In embodiments, an application presents to the user 205 a drawing on the touch-sensitive screen of the user device 215. The user 205 then attempts to trace the drawing, which may be a simple line or a circle, or a more complicated figure. The pattern produced by the user is then transmitted to the server 220, which compares it to the drawing presented to the user. Alternatively, only the differences between the drawing and the user-produced pattern are sent to the server 220. In yet another alternative, the user device 215 generates a metric from the differences between the drawing and the pattern, and transmits the metric to the server 220. The server 220 processes these data from the application to determine whether a trigger event has occurred. For example, as recited in U.S. Provisional Application No. 61/299,568, the user may trace a line. The drawing or tracing of a test may be done by the user's finger, stylus, or some other device that allows input as to the user's tracing of the line or symbol. In this embodiment the test may be set for a number of times in which the user would trace the complete line. Or another setting may be a limited amount of time in which the user may trace the line as many times as possible. In an embodiment, an audio sound, bell or other signal may be present to communicate a complete trace of the entire length of the line. A complete trace of the line being defined as a drawing or tracing the "trace line" to touching or exceeding the boundary lines that visually define the end points of the "trace line". Once a boundary line is touched an audio or visual signal (such as the boundary line changing color) may be utilized.

In another embodiment, the user may be required to draw or write their name or some other combination of words or phrases. The user may be required to draw or write their name on a blank or empty space of the screen, or may be required to trace their name or words.

In an embodiment, there may be a results screen that contains detailed information about a specific test. This detailed information may include test date, test time, which hand was used, whether there was a timer setting and what the time was set at, the number of laps or iterations of drawing, and other configuration options and information. Test result information may contain quantitative results resulting from the analysis of the user's performance during the test. Quantitative results may include the measurement of the amplitude or deviation from the trace line as discussed in the article:

"Tremor amplitude as logarithmically related to 4 and 5-point Tremor rating scales, published brain advance access Aug. 3, 2006".

Additional information may include numeric and quantitative comparisons with previous tests, comparative information, data asked to number of points of intersection between the drawing or tracing and the trace line, and other quantitative points of measurement. The embodiment may also include the ability to view an image of the test results. The test result page may also contain the option to manually send the test results to a third party by attaching and including it in an e-mail, XML, put or call, or some other means of transporting the information.

In embodiments, the user device 215 includes an acceleration, vibration, or shock sensor. An application requests the user to hold the device steady in hand, without support. The application then measures acceleration/vibrations of the device 215, and transmits the results (such as actual vibration measurements or a metric derived from the vibration measurements) to the server 220. The server 220 processes these data from the application to determine whether a trigger event has occurred. Similarly, the user device 215 may be used to measure range of motion for a joint(s) or movement. For example, as recited in U.S. Provisional Application No. 61/321,568, in an embodiment, a single accelerometer sensor enabled device is utilized to obtain these measurements. In this embodiment the enabled device could be employed to detect the absolute degrees of the movement of an object. Specifically, the device may be held, or attached against the object to be monitored with the measuring sensor's axis parallel to the object to be in measured and in the plane of the objects motion. At the initiation of the measurement of the device records the axis vector through its relative position in degrees to the force of gravity. The movement or motion to be measured is then initiated. Once completed, the embodiment records the new axis vector and its relative position in degrees. The absolute difference between these two measurements quantifies the range of motion in degrees. The information provided to the user sets the initial vector equal to zero, or "zero starting point" where the degrees of that position are displayed at zero. All motions of a joint are measured from defined zero starting point positions. The degrees of motion of a joint are added in the direction the joint moves from the zero starting position. The final number displayed is the degrees of motion/movement.

In an embodiment, the application can utilize a device with three accelerometers to measure movement of an object in a three dimensional space. The device with a three axis sensor that would be attached, mounted, held against, or otherwise placed in contact with the object of which movement is to be measured. The three axis sensor would be utilized to determine the beginning vector of the object by measuring the angle of each of the three axis as compared to a horizontal plane. The beginning vector is determinate and recorded, and the object then completes the movement to be measured. Once again the object's vector is determined and recorded. The angles of each axis are measured to establish the object's final relative vector to a horizontal plane. The distance in degrees between the two vectors is the measurement of the object's range of movement.

In an embodiment, a graphical representation of the objects being measured could be utilized as a menu to record which object is being measured. For example there may be a drawing of a body of which the user would select which body part or joint is being measured. Then perform the measurement and the resulting data would be paired with identification of the proper joint being measured. This graphical interface could be utilized for other types of measurements, surveys, and tests. Such as enabling a user to touch the graphical representation to indicate where a pain is.

In an embodiment the menu system may be a graphic representation of the various parts of an object that can be measured. In this embodiment there is a graphical representation of the human body. This graphic representation is displayed upon a touch sensitive screen and may be mapped so that when an area of the screen is touched a separate menu item is selected. Each menu item when touched can indicate a specific area that is going to be measured or a general area to select a submenu of various items that may be measured. Upon selecting that area on the larger main graphic interface, a detailed graphic menu of that area may then be displayed. This graphic submenu may identify specific objects that the user may use the device to measure. In this example the user may select a specific joint (e.g. the first joint of the index finger) and the device will record that selection then proceed to the testing interface where the actual test may be run. At that point the recorded identification of the joints and specific object being measured is paired with the results of the tests. This allows the automatic pairing of test results with the identification of the joint or specific object being measured. In addition an embodiment may choose a specific axis to be utilized with specific menu choices or selected objects to be measured. The selected axis may be a single axis or multiple axis. The graphical menu interface may be utilized in capturing other data, tests, surveys, and applications. For example it may be paired with a survey where the user is asked to point to and select an area of pain.

Similarly, the user device 215 may be used to perform a vision test. For example, as recited in U.S. Provisional Application No. 61/298,068, in an embodiment, moving patterns and symbols are displayed on a screen of the user device 215 to elicit rhythmic eye movements called nystagmus. In an embodiment, alternating lines of color or black-and-white or shapes across scrolls the screen to elicit either movements as the user's eye tracks the moving field.

In an embodiment, a vision drum test is performed where alternating lines of black-and-white moving across the screen at a rapid pace. The intent is to elicit eye movement from the user as they watched the screen. The resulting eye movements can be utilized to determine or diagnose various conditions.

In an embodiment, color saturation test is performed where a solid red screen and a solid green screen are displayed. With this component the user will cover one eye and look at the colored screen and then in turn cover the other and look at the screen. If the colors appear different to the user that may assist in identifying or evaluating issues.

In an embodiment, a visual acuity test is performed where quantitative measurement of the user's ability to identify black symbols or letters on a white background at a standardized distance as the size or position of the symbols or letters vary. The user's visual acuity can be measured and compared to the population or compared to other test of the user longitudinally.

In an embodiment, a color sensitivity test is performed which integrates Ishihara plates in an interactive means, which can provide quantitative measurement as to the users color sensitivity.

Similarly, the user device 215 may be used to perform a reactive response test. For example, as recited in U.S. Provisional Application No. 61/295,917, in an embodiment, an initial button may be placed randomly on the touch screen area of device 215 designated. In an embodiment once a tap on the screen is made the button disappears and is displayed in another random location. The sequence of button movement is repeated until the allotted time has transpired. In another embodiment a button does not change location until it has been tapped successfully. In an embodiment when a button is successfully tapped success is signaled with an audio sound. If the tap is unsuccessful a different audio sound is signaled. In an embodiment a successful or unsuccessful tap may be signaled by a change in color, shape, or size of the button itself.

In an embodiment there may be an options or configuration screen in which variables, permutations, in various options for various embodiments may be implemented, modified, or set. In an embodiment a configuration option may include the ability for the user to turn the display of the timer and/or the counter on or off during a test. In an embodiment a user could select to have the button move with every tap or for only successful taps. In another embodiment the user can select a simple reaction time option that enables a test in which the button on the test screen is tapped where the intent of the test is to measure reaction time of the user. In another embodiment the user may select different size buttons to be utilized in a test. In an embodiment the user or third-party may set the length of time the test will run.

Similarly, the user device 215 may be used to perform a motor control test. For example, as recited in U.S. Provisional Application No. 61/295,104, in an embodiment, a user device 215 includes a touch sensitive screen with a graphic or otherwise highlighted area of the screen to be touched or tapped by the user with a number of taps or touches during a specified time.

In an embodiment a timer may display the time remaining out of a current test, or how much time has progressed during a current test. In another embodiment, a counter may be present to display the number of taps or touches that have occurred during the current test that is being performed, or the most recently completed test.

In another embodiment of the invention a button, graphic, or icon may be used to record which hand or foot will be utilized to perform the next test, or is being utilized in the current test. Another embodiment includes a menu with multiple buttons.

An embodiment may have an input button. Once a test begins the user device 215 records the number of touches or taps of the button for the duration of the test. In one embodiment the time does not begin counting until the button is tapped or touched for the first time after a test is initiated. In another embodiment the counter begins immediately upon beginning to test. In an embodiment the test may be ran with the user utilizing their left or right hand. A successful tap or touch may be reflected in an audio sound such as a bill or 'click', or in a visual cue such as the button changing color, shape, or appearance. The button's changing appearance may reflect the appearance to a physical button being depressed.

In an embodiment there may be an options or configuration screen in which variables, permutations, in various options for various embodiments may be implemented, modified, or set. In an embodiment a configuration option may include the ability for the user to turn the display of the timer and/or the counter on or off during a test. In an embodiment a user could select to display a single button for the test or two buttons for utilization by a right and left or by two fingers of the same hand. In another embodiment the user can select a simple reaction time option that enables a test in which the button on the test screen is tapped just once in a response to a signal such as a sound or a changing color of the button. The intent of this test is to measure reaction time of the user. In another embodiment the user may select different size buttons to be utilized in a test in which the user taps the button with their finger or their toe. In an embodiment the user or third-party may set the length of time the test will run.

In an embodiment there may be two buttons available for the test. The two buttons may be utilized in a test in which the user would tap one button with their left hand and the second button with their right hand. Another embodiment may include testing utilizing two buttons to be pressed alternatively with two different fingers of the same hand.

As recited in U.S. Provisional Application No. 61/295,917, in an embodiment detailed information about the results of a test may be presented. Detailed information may include information about the individual test which may include the user's name, identification, biographical information and other information. In an embodiment there may be included detailed information about a recent specific test which may include test results, as well as test settings, options, date, location of test (including latitude and longitude) address, default language, time zone, time and other information. In an embodiment there may be summarized information of past tests for example including number of tests taken, average results, frequency of tests, first tests performed, last tests performed, default options, default configurations, and other information. In another embodiment a detailed results screen may include comparative information and data between the recent or past tests and averages, mediums and other statistical information. In another embodiment there may be included longitudinal information which may displayed in a graphical format showing trends, results over time. In another embodiment other numeric and visually means of communicating results information and other data may be included. In another embodiment 3rd parties who had received or viewed the results could be tracked which could include individuals, organizations, or devices that results were sent to, access by or shared with. This tracking of access by individuals or third parties or the user may include information about who accessed, what information they accessed, authentication codes, addresses, identification, times and date of access, means of access (i.e. visual on device, remotely through phone, internet or other means) and restrictions.

As part of each medical test, the application may obtain some form of verification of the identity of the user 205. For example, the application may guide the user through performing a fingerprint scan with a camera or a scanner of the user device 215, taking the user's picture with the camera, or obtaining the user's signature on the screen of the user device 215. In embodiments, the verification is performed at the server 220, which compares the biometric data to the corresponding sample previously stored on the server 220 or on the device 215. The application transmits to the server 220 the time of the identity verification, together with the biometric or other security-verifying data. In embodiments, the verification is performed at the server 220 after the application transmits the verification data (e.g., the user's scanned fingerprint, scanned signature, picture) together with the test data. The server 220 then performs the verification by comparing the verification data transmitted with the corresponding sample stored on the server 220. The sample may be obtained at the time of the user's registration with the server 220 or with the third party 210. If the verification data does not match the sample stored on the server 220 or the user device 215, the user may be asked to repeat the verification and the test.

Figure 5:
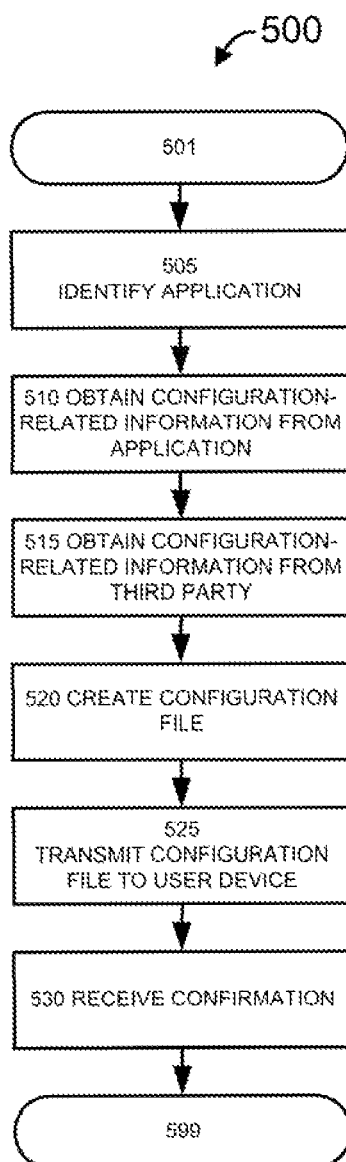
FIG. 5 illustrates selected steps of a process for creating or modifying a configuration file for an application on a user device.

FIG. 5 illustrates selected steps and decisions of an exemplary process 500 through which the server 220 creates or modifies a configuration file for an application on the device 215.

At a flow point 501, the server 220 is running and configured to communicate with the user device 215.

In step 505, the server 220 receives an identification of the application on the device 215. The server 220 may first request the identification of the application, or the application may initiate communications with the server 220 and inform the server 220 of its identity.

In step 510, the server 220 receives from the application the current configuration-related information of the application. The configuration-related information obtained from the application may include the configuration file already on the user device 215 (if the file exists), the responses to survey(s)/questionnaire(s) that the application obtained from the user 205, and identifiers of the hardware and software of the device 215. The server 220 may first request such configuration-related information from the application, or the application may initiate communications with the server 220 and provide the server 220 the configuration-related information without a prior request.

In step 515, the server 220 obtains configuration-related information from the third party 210, which may include specific instructions for inclusion and/or exclusion of configuration requirements and limitations in the configuration file. The server 220 may first request such configuration-related information from the third party 210, or the third party 210 (or the third party device 230, or yet another device associated with the third party) may provide the server 220 the configuration-related information without a prior request. If the server 220 requests the configuration-related information from the third party 210 (or the third party device 230, or yet another device), the request may contain data from the configuration-related information the server 220 obtained from the application. In embodiments, however, the server 220 obtains the configuration-related information from the third party 210 or its device 230 before obtaining the configuration-related information from the user device 215; in such embodiments, the request to the application for the configuration-related information may include data from the configuration-related information obtained from the third party 210 (or its device 230 or yet another device).

The server 220 may store the information received in the steps 505, 510, and 515 in its database 160.

In step 520, the server 220 engages its rules-based engine algorithm to create the configuration file for the application on the user device 215, based on the information obtained in the steps 505, 510, and 515, and possibly other information. In examples, the old configuration file (obtained from the user device 215) is supplemented with additional information to create the new configuration file in this step. In examples, information is deleted from the old configuration file to create the new configuration file in this step. In examples, information is deleted from the old configuration file and then the resulting file is supplemented with additional information to create the new configuration file in this step.

In step 525, the server 220 transmits the new or modified configuration file to the user device 215.

In step 530, the server receives one or more messages from the user device 215 confirming that the user device 215 has received the configuration file and is ready to use it.

Process flow then terminates at a flow point 599.

Figure 6:
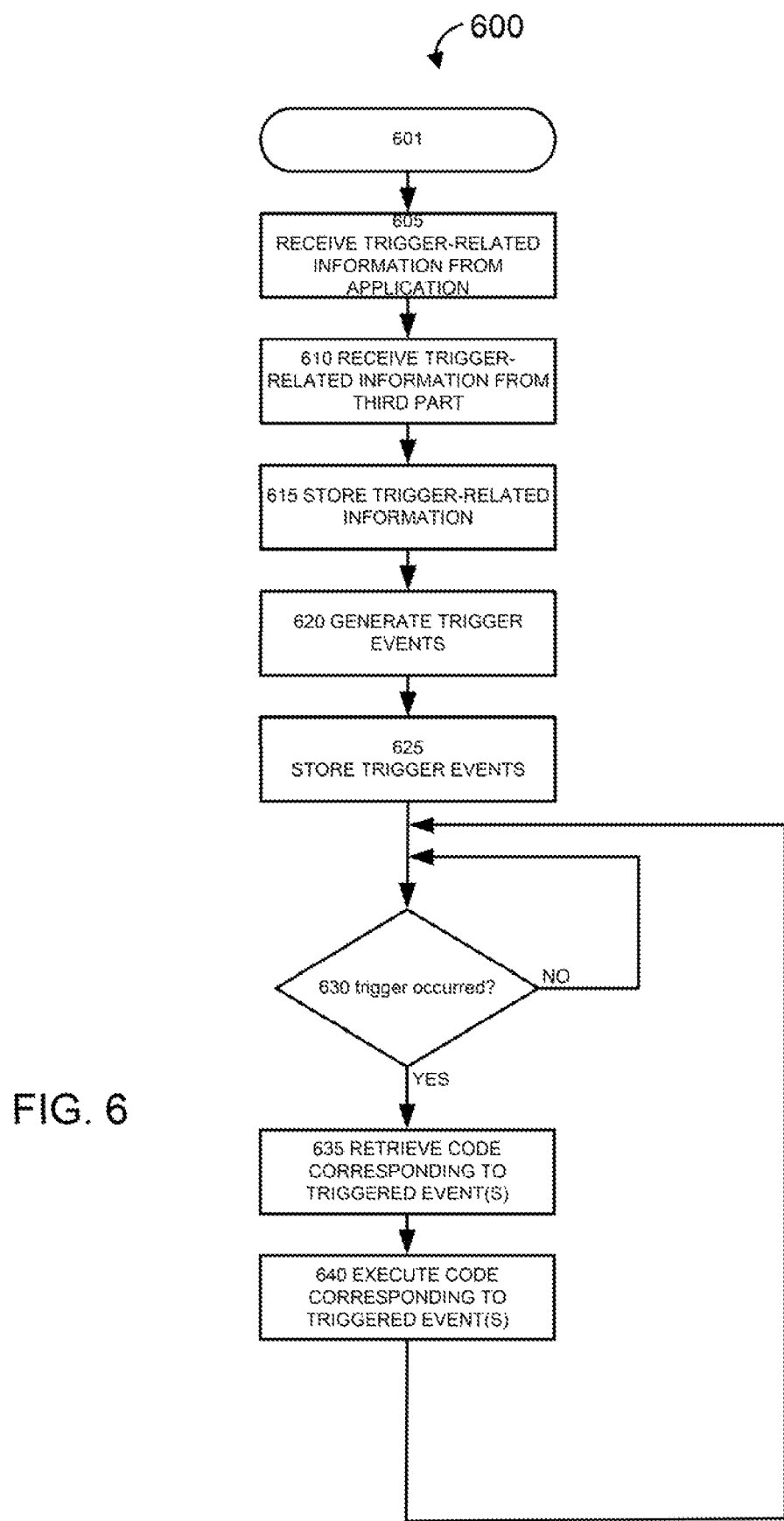
FIG. 6 illustrates selected steps and decisions of a process for creating or modifying a trigger event, and acting on the trigger event.

FIG. 6 illustrates selected steps and decisions of an exemplary process 600 through which the server 220 creates or modifies a trigger event, and then acts when the trigger event occurs.

At a flow point 601, the server 220 is running and has been configured to communicate with an application on the user device 215. The application has been configured, for example, as has been described above in relation to the process 500. Note, however, that some of the steps (or parts of the steps) of the process 600 may be performed as part of the process 500.

In step 605, the server 220 receives trigger-related information from the application, such as preferences of the user 205 for setting trigger events, scheduled times for events, and actual trigger values or other conditions for triggering the events.

In step 610, the server 220 receives trigger-related information from the third party 205 (or its device 230, or yet another device). This trigger-related information may be the same as the trigger-related information described in relation to the step 605.

In step 615, the server 220 stores the trigger-related information received in the steps 605 and 610.

In step 620, the server 220 engages a trigger generator to generate one or more trigger events and tasks corresponding to the one or more trigger events. The trigger generator may be a rules-based engine that processes the trigger-related information and other information received by the server 220.

In step 625, the server 220 stores the generated trigger events.

In decision block 630, the server 220 monitors information sources that may trigger the stored trigger events. For example, the server 220 periodically compares the current time with the time of the scheduled events, and reviews the data received from the user device 220 to determine whether the data correspond to one of the trigger events. As long as no trigger event takes place, the decision block 630 loops on itself. When a trigger event takes place, process flow proceeds to step 635.

In the step 635, the server 220 retrieves code of the task corresponding to the triggered event.

In step 640, the server 220 executes the task corresponding to the trigger event. As discussed above, the task may include a notification and a change to the configuration file(s) for the application and/or other applications on the user device 215.

Process flow then returns to the decision block 630, to monitor the information sources that may trigger the stored trigger events.

The processes 500 and 600 may be performed, in whole or in part, by the system 100 of FIG. 1, for example. Although the process steps and decisions are described serially, certain steps and decisions may be performed by separate elements in conjunction or in parallel, asynchronously or synchronously, in a pipelined manner, or otherwise. There is no particular requirement that the steps and decisions be performed in the same order in which this description lists them, except where a specific order is inherently required, explicitly indicated, or is otherwise made clear from the context. Furthermore, not every illustrated step and decision block may be required in every embodiment in accordance with the invention, while some steps and decision blocks that have not been specifically illustrated, may be desirable or necessary in some embodiments in accordance with the invention.

Various embodiments, variants, and examples have been described above. We contemplate all possible combinations of two or more of the embodiments, variants, and examples, unless a combination is specifically excluded, is internally inconsistent, or otherwise impossible to implement.

The various illustrative logical blocks, modules, and steps described in this document may be implemented in the form of electronic hardware, software, firmware, or combinations of hardware, software, and firmware. Whether the functionality of the blocks, modules, and steps is implemented as hardware, software, firmware or combination of these may be implementation choices. Such implementation choices should not be interpreted as necessarily causing a departure from the scope of the present specification.

The various illustrative logical blocks, modules, and steps described herein may be implemented with a general purpose processor, a signal processor, an application specific integrated circuit (ASIC), and other logic devices, both integrated and discrete, and combination thereof.

The software and firmware storing machine-readable code with instructions for performing the steps described in this document may be stored in RAM memory, flash memory, ROM memory, EPROM memory, EEPROM memory, registers, hard disk, removable disk, CD-ROM, or any other form of storage medium known in the art. The code may also be transmitted wirelessly, over wires, through fiberoptic lines, or otherwise.

This document describes in considerable detail the inventive apparatus, methods, and articles of manufacture for performing medical surveillance through a general-purpose personal communication device. This was done for illustration purposes only. Neither the specific embodiments of the invention as a whole, nor those of its features, necessarily limit the general principles underlying the invention. The specific features described herein may be used in some embodiments, but not in others, without departure from the spirit and scope of the invention as set forth herein. Various physical arrangements of components and various step sequences also fall within the intended scope of the invention. Many additional modifications are intended in the foregoing disclosure, and it will be appreciated by those of ordinary skill in the art that. in some instances, some features may be employed in the absence of a corresponding use of other features. The illustrative examples therefore do not necessarily define the metes and bounds of the invention. It follows that the illustrative examples do not necessarily define the legal protection afforded the invention, which function is carried out by the claims that may issue on this application and its related applications, and their equivalents.

We claim:

1. A method for sharing medical data between applications on a user device, the method comprising:
    maintaining a data store on the user device;
    executing an initialization application on the user device, the initialization application being configured to manage a plurality of configuration files corresponding to a plurality of applications on the user device, each of the configuration files comprising one or more key value pairs, each key value pair comprising identifying data matched with data that defines an operating parameter for at least one of the plurality of applications;
    executing a first application of the plurality of applications based on a first configuration file of the plurality of configuration files, the first configuration file including a first key value pair that defines an access level to the data store;
    executing a second application of the plurality of applications based on a second configuration file of the plurality of configuration files, the second application being different than the first application, the second configuration file including a second key value pair that defines an access level to the data store;
    storing, by the first application, medical data in the data store based on the access level defined by the first key value pair;
    accessing, by the second application, the medical data in the data store based on the access level defined by the second key value pair;
    performing a medical test for a user with the user device;
    determining a metric based on the medical test; and
    triggering an event based on a comparison of the medical test to a threshold, wherein the event comprises sending information indicative of the comparison to a computing device.

2. The method of claim 1, wherein the initialization application is one of the first application and the second application.

3. The method of claim 1, wherein accessing comprises modifying, deleting, or augmenting depending on the access level defined by the second key value pair.

4. The method of claim 1, wherein at least one of the one or more key value pairs comprises data values restricted to a range or type.

5. The method of claim 1, wherein at least one of the plurality of configuration files comprises an extended markup language formatted file.

6. The method of claim 1, wherein the first key value pair defines a security parameter, and wherein the first application encrypts the stored medical data based on the security parameter.

7. The method of claim 1, further comprising modifying the second configuration file by the initialization application to change an access level of the second application to the data store.

8. A method for sharing medical data between applications on a user device, the method comprising:
    maintaining a data store on the user device;
    executing an initialization application on the user device, the initialization application being configured to manage a plurality of configuration files corresponding to a plurality of applications on the user device, each of the configuration files comprising one or more key value pairs, each key value pair comprising identifying data matched with data that defines an operating parameter for at least one of the plurality of applications;
    executing a first application of the plurality of applications based on a first configuration file of the plurality of configuration files, the first configuration file including a first key value pair that defines an access level to the data store;
    executing a second application of the plurality of applications based on a second configuration file of the plurality of configuration files, the second application being different than the first application, the second configuration file including a second key value pair that defines an access level to the data store;
    storing, by the first application, medical data in the data store based on the access level defined by the first key value pair;
    accessing, by the second application, the medical data in the data store based on the access level defined by the second key value pair;
    receiving an input on a touch screen of the user device corresponding to a tracing of a pattern by the first application;
    determining a deviation of the tracing from the pattern; and
    triggering an event based on a comparison of the deviation to a threshold.

9. A method for sharing medical data between applications on a user device, the method comprising:
    maintaining a data store on the user device;
    executing an initialization application on the user device, the initialization application being configured to manage a plurality of configuration files corresponding to a plurality of applications on the user device, each of the configuration files comprising one or more key value pairs, each key value pair comprising identifying data matched with data that defines an operating parameter for at least one of the plurality of applications;
    executing a first application of the plurality of applications based on a first configuration file of the plurality of configuration files, the first configuration file including a first key value pair that defines an access level to the data store;
executing a second application of the plurality of applications based on a second configuration file of the plurality of configuration files, the second application being different than the first application, the second configuration file including a second key value pair that defines an access level to the data store;
storing, by the first application, medical data in the data store based on the access level defined by the first key value pair;
accessing, by the second application, the medical data in the data store based on the access level defined by the second key value pair;
measuring movement of the user device using a sensor in the user device while a user holds the user device;
determining a movement metric based on the measured movement; and
triggering an event based on a comparison of the movement metric to a threshold.

10. The method of claim 1, further comprising:
performing a verification of an identity of the user, wherein triggering the event is further based on verification of the identification of the user.

11. The method of claim 1, wherein the event comprises preventing display of results of the medical test.

12. A method for sharing medical data between applications on a user device, the method comprising:
maintaining a data store on the user device;
executing an initialization application on the user device, the initialization application being configured to manage a plurality of configuration files corresponding to a plurality of applications on the user device, each of the configuration files comprising one or more key value pairs, each key value pair comprising identifying data matched with data that defines an operating parameter for at least one of the plurality of applications;
executing a first application of the plurality of applications based on a first configuration file of the plurality of configuration files, the first configuration file including a first key value pair that defines an access level to the data store;
executing a second application of the plurality of applications based on a second configuration file of the plurality of configuration files, the second application being different than the first application, the second configuration file including a second key value pair that defines an access level to the data store;
storing, by the first application, medical data in the data store based on the access level defined by the first key value pair;
accessing, by the second application, the medical data in the data store based on the access level defined by the second key value pair;
performing a medical test for a user with the user device;
determining a metric based on the medical test; and
triggering an event based on a comparison of the medical test to a threshold, wherein the medical test comprises a vision test, and wherein performing the test comprises measuring the timing of areas touched on a touch screen related to graphics displayed on the touch screen of the user device.

13. A method for sharing medical data between applications on a user device, the method comprising:
maintaining a data store on the user device;
executing an initialization application on the user device, the initialization application being configured to manage a plurality of configuration files corresponding to a plurality of applications on the user device, each of the configuration files comprising one or more key value pairs, each key value pair comprising identifying data matched with data that defines an operating parameter for at least one of the plurality of applications;
executing a first application of the plurality of applications based on a first configuration file of the plurality of configuration files, the first configuration file including a first key value pair that defines an access level to the data store;
executing a second application of the plurality of applications based on a second configuration file of the plurality of configuration files, the second application being different than the first application, the second configuration file including a second key value pair that defines an access level to the data store;
storing, by the first application, medical data in the data store based on the access level defined by the first key value pair;
accessing, by the second application, the medical data in the data store based on the access level defined by the second key value pair;
performing a medical test for a user with the user device;
determining a metric based on the medical test; and
triggering an event based on a comparison of the medical test to a threshold, wherein the medical test comprises a motor skill test, and wherein performing the test comprises measuring an accuracy and timing of areas touched on a touch screen related to graphics displayed on the touch screen of the user device.

14. The method of claim 1, wherein the initialization application manages the plurality of configuration files based on an identification code received on the user device.

15. The method of claim 1, wherein the operating parameter comprises a configuration for a menu of at least one of the plurality of applications.

16. A user device configured to share medical data between applications on the user device, the user device comprising:
a memory comprising a data store; and
a processor configured to:
execute an initialization application on the user device, the initialization application being configured to manage a plurality of configuration files corresponding to a plurality of applications on the user device, each of the configuration files comprising one or more key value pairs, each key value pair comprising identifying data matched with data that defines an operating parameter for at least one of the plurality of applications;
execute a first application of the plurality of applications based on a first configuration file of the plurality of configuration files, the first configuration file including a first key value pair that defines an access level to the data store;
execute a second application of the plurality of applications based on a second configuration file of the plurality of configuration files, the second application being different than the first application, the second configuration file including a second key value pair that defines an access level to the data store;

store, by the first application, medical data in the data store based on the access level defined by the first key value pair;
access, by the second application, the medical data in the data store based on the access level defined by the second key value pair;
perform a medical test for a user with the user device;
determine a metric based on the medical test; and
trigger an event based on a comparison of the medical test to a threshold, wherein the event comprises sending information indicative of the comparison to a computing device.

17. The user device of claim 16, wherein the first key value pair defines a security parameter, and wherein the first application encrypts the stored medical data based on the security parameter.

18. The user device of claim 16, wherein the processor is further configured to modify the second configuration file by the initialization application to change an access level of the second application to the data store.

19. A user device configured to share medical data between applications on the user device, the user device comprising:
a memory comprising a data store; and
a processor configured to:
execute an initialization application on the user device, the initialization application being configured to manage a plurality of configuration files corresponding to a plurality of applications on the user device, each of the configuration files comprising one or more key value pairs, each key value pair comprising identifying data matched with data that defines an operating parameter for at least one of the plurality of applications;
execute a first application of the plurality of applications based on a first configuration file of the plurality of configuration files, the first configuration file including a first key value pair that defines an access level to the data store;
execute a second application of the plurality of applications based on a second configuration file of the plurality of configuration files, the second application being different than the first application, the second configuration file including a second key value pair that defines an access level to the data store;
store, by the first application, medical data in the data store based on the access level defined by the first key value pair;
access, by the second application, the medical data in the data store based on the access level defined by the second key value pair;
receive an input on a touch screen of the user device corresponding to a tracing of a pattern by the first application;
determine a deviation of the tracing from the pattern; and
trigger an event based on a comparison of the deviation to a threshold.

20. A user device configured to share medical data between applications on the user device, the user device comprising:
a memory comprising a data store; and
a processor configured to:
execute an initialization application on the user device, the initialization application being configured to manage a plurality of configuration files corresponding to a plurality of applications on the user device, each of the configuration files comprising one or more key value pairs, each key value pair comprising identifying data matched with data that defines an operating parameter for at least one of the plurality of applications;
execute a first application of the plurality of applications based on a first configuration file of the plurality of configuration files, the first configuration file including a first key value pair that defines an access level to the data store;
execute a second application of the plurality of applications based on a second configuration file of the plurality of configuration files, the second application being different than the first application, the second configuration file including a second key value pair that defines an access level to the data store;
store, by the first application, medical data in the data store based on the access level defined by the first key value pair;
access, by the second application, the medical data in the data store based on the access level defined by the second key value pair;
measure movement of the user device using a sensor in the user device while a user holds the user device;
determine a movement metric based on the measured movement; and
trigger an event based on a comparison of the movement metric to a threshold.

21. The user device of claim 16, wherein the processor is further configured to:
perform a verification of an identity of the user, wherein triggering the event is further based on verification of the identification of the user.

22. The user device of claim 16, wherein the event comprises preventing display of results of the medical test.

23. A user device configured to share medical data between applications on the user device, the user device comprising:
a memory comprising a data store; and
a processor configured to:
execute an initialization application on the user device, the initialization application being configured to manage a plurality of configuration files corresponding to a plurality of applications on the user device, each of the configuration files comprising one or more key value pairs, each key value pair comprising identifying data matched with data that defines an operating parameter for at least one of the plurality of applications;
execute a first application of the plurality of applications based on a first configuration file of the plurality of configuration files, the first configuration file including a first key value pair that defines an access level to the data store;
execute a second application of the plurality of applications based on a second configuration file of the plurality of configuration files, the second application being different than the first application, the second configuration file including a second key value pair that defines an access level to the data store;
store, by the first application, medical data in the data store based on the access level defined by the first key value pair;

access, by the second application, the medical data in the data store based on the access level defined by the second key value pair;

perform a medical test for a user with the user device;

determine a metric based on the medical test; and trigger an event based on a comparison of the medical test to a threshold, wherein the medical test comprises a vision test, and wherein performing the test comprises measuring the timing of areas touched on a touch screen related to graphics displayed on the touch screen of the user device.

24. A user device configured to share medical data between applications on the user device, the user device comprising:

a memory comprising a data store; and a processor configured to:

execute an initialization application on the user device, the initialization application being configured to manage a plurality of configuration files corresponding to a plurality of applications on the user device, each of the configuration files comprising one or more key value pairs, each key value pair comprising identifying data matched with data that defines an operating parameter for at least one of the plurality of applications;

execute a first application of the plurality of applications based on a first configuration file of the plurality of configuration files, the first configuration file including a first key value pair that defines an access level to the data store;

execute a second application of the plurality of applications based on a second configuration file of the plurality of configuration files, the second application being different than the first application, the second configuration file including a second key value pair that defines an access level to the data store;

store, by the first application, medical data in the data store based on the access level defined by the first key value pair;

access, by the second application, the medical data in the data store based on the access level defined by the second key value pair;

perform a medical test for a user with the user device;

determine a metric based on the medical test; and trigger an event based on a comparison of the medical test to a threshold, wherein the medical test comprises a motor skill test, and wherein performing the test comprises measuring an accuracy and timing of areas touched on a touch screen related to graphics displayed on the touch screen of the user device.

25. The user device of claim 16, wherein the initialization application manages the plurality of configuration files based on an identification code received on the user device.

26. A non-transitory computer-readable medium comprising instructions that when executed by a computing device cause the computing device to perform a method for sharing medical data between applications on a user device, the method comprising:

maintaining a data store on the user device;

executing an initialization application on the user device, the initialization application being configured to manage a plurality of configuration files corresponding to a plurality of applications on the user device, each of the configuration files comprising one or more key value pairs, each key value pair comprising identifying data matched with data that defines an operating parameter for at least one of the plurality of applications;

executing a first application of the plurality of applications based on a first configuration file of the plurality of configuration files, the first configuration file including a first key value pair that defines an access level to the data store;

executing a second application of the plurality of applications based on a second configuration file of the plurality of configuration files, the second application being different than the first application, the second configuration file including a second key value pair that defines an access level to the data store;

storing, by the first application, medical data in the data store based on the access level defined by the first key value pair;

accessing, by the second application, the medical data in the data store based on the access level defined by the second key value pair;

performing a medical test for a user with the user device;

determining a metric based on the medical test; and triggering an event based on a comparison of the medical test to a threshold, wherein the event comprises sending information indicative of the comparison to a computing device.

* * * * *